United States Patent [19]

Grasel et al.

[11] Patent Number: 5,017,664
[45] Date of Patent: May 21, 1991

[54] BIOCOMPATIBLE POLYURETHANE DEVICES WHEREIN POLYURETHANE IS MODIFIED WITH LOWER ALKYL SULFONATE AND LOWER ALKYL CARBOXYLATE

[75] Inventors: Timothy G. Grasel; Stuart L. Cooper, both of Madison, Wis.

[73] Assignee: Wisconsin Alumni Research Foundation, Madison, Wis.

[21] Appl. No.: 333,991

[22] Filed: Apr. 5, 1989

Related U.S. Application Data

[62] Division of Ser. No. 57,546, Jun. 3, 1987, Pat. No. 4,880,883.

[51] Int. Cl.$^5$ .................. C08G 18/82; C08G 18/87
[52] U.S. Cl. ........................... 525/454; 528/49; 528/71; 604/266
[58] Field of Search ............ 525/454; 528/49, 71; 604/266

[56] References Cited

U.S. PATENT DOCUMENTS

| 3,903,032 | 9/1975 | Matsuda et al. | 528/71 |
| 4,237,250 | 12/1980 | Dieterich | 525/454 |
| 4,276,044 | 6/1981 | Dieterich | 528/71 |
| 4,303,774 | 12/1981 | Machtkamp et al. | 528/71 |
| 4,503,198 | 3/1985 | Miyai et al. | 528/71 |
| 4,579,930 | 4/1986 | Kramer et al. | 528/71 |
| 4,670,330 | 6/1987 | Ishiwata | 528/71 |
| 4,675,361 | 6/1987 | Ward, Jr. | 525/454 |
| 4,689,386 | 8/1987 | Chapman et al. | 528/71 |
| 4,831,065 | 5/1989 | Pietsch et al. | 525/454 |

OTHER PUBLICATIONS

Lelah et al., "Polyether-Urethane Ionomers Surface Property/Ex Vivo Blood Compatibility Relationships", J. Coll. Interf. Sci., 104, 422–439 (1985) (Article I).
Lelah et al., "Ex Vivo Interactions and Surface Property Relationships of Polyetherurethanes," J. Biomed. Mater. Res., 20 433–468 (1986) (Article II).
Hwang et al., "Properties of Polyurethane Anionomers: Ionization via Bimolecular Nucleophilic Displacement of Urethane Hydrogen,", J. Macromol. Sci.-Phys., B23, 154–174 (1984).

Primary Examiner—Morton Foelak
Assistant Examiner—Dennis R. Daley
Attorney, Agent, or Firm—Olson & Hierl

[57] ABSTRACT

Modified-polyurethane block copolymers and devices formed therefrom demonstrate excellent biocompatibilty and improved physical and mechanical properties. In a preferred embodiment, from about 5 to about 25 percent of urethane hydrogen atoms are replaced with propyl sulfonate and propyl carboxylate groups to provide the modified copolymer.

12 Claims, 14 Drawing Sheets

5'

15'

30'

60'

PEU

5'

15'

30'

60'

PEU-SO3-0.10

5'

15'

30'

60'

PEU-SO3-0.20

PEU-SO3-0.15

30'

BIOCOMPATIBLE POLYURETHANE DEVICES WHEREIN POLYURETHANE IS MODIFIED WITH LOWER ALKYL SULFONATE AND LOWER ALKYL CARBOXYLATE

This invention was made with United States Government support awarded by the National Institutes of Health (NIH), Grant Number: HL 24046. The United States Government has certain rights in this invention.

This application is a division of application Ser. No. 057,546, filed June 3, 1987, now U.S. Pat. No. 4,880,883.

TECHNICAL FIELD OF THE INVENTION

This invention relates to polyurethanes and, in particular, to polyurethane block copolymers which demonstrate excellent biocompatibility and improved physical and mechanical properties.

BACKGROUND OF THE INVENTION

The properties of a polymer are of great importance in any application. For biomedical polymers, the most important single property is probably biocompatibility, which refers to the interactions of living body tissues, compounds and fluids including blood with any implanted or contacting polymeric material. Each system of polymer-body tissue interactions must be studied individually in terms of polymer stability, general tissue-fluid interactions and blood compatibility.

Polyurethane block copolymers have been proposed for use in blood-contacting applications because of their generally excellent physical properties and relatively good blood compatibility. Lelah and Cooper, *Polyurethanes in Medicine*, CRC Press, Boca Raton, Fla. (1986). It is desirable however, to further improve the blood compatibility of these materials to allow their use in such demanding applications as small-diameter vascular grafts, catheters, kidney dialyzers, cardiac assist devices and the artificial heart.

Thrombus formation on polyurethanes and other blood-contacting biomaterials can lead to occlusion of vascular grafts or catheters, and detachment (embolization) of these thrombi may result in tissue damage or strokes. Several approaches have been proposed for improving the blood compatibility of blood-contacting biomaterials. One method involves the preparation of a highly hydrophilic, mobile interface comprising materials that appear "bland" to blood components. Merrill et al., *Am. Soc. Artif. Intern. Organs J.*, 6, 60 (1983). These "bland" materials may demonstrate a reduced tendency for protein absorption and platelet adhesion.

Another method involves the introduction of highly hydrophobic groups to the blood-contacting interface, either by using a highly hydrophobic polymer such as silicone rubber or by grafting long alkyl chains to a relatively hydrophilic material, such as a polyurethane block copolymer. By using long-chain alkyl grafting methods, Eberhart and coworkers [Munro, et al., *Am. Soc. Artif. Intern. Organs J.*, 6, 65 (1983)] have improved the blood compatibility of polyurethane block copolymers. Similar approaches have resulted in the reduction of platelet and fibrinogen deposition in canine ex vivo blood-contacting studies.

A third method involves incorporating ionic character into the polymer. This approach may also result in a highly hydrophilic and mobile interface which has a low driving force for protein adsorption and cell adhesion. In fact, many researchers have used this approach in an attempt to provide a surface that will initiate the anti-coagulant action of heparin, a highly ionic mucopolysaccharide.

The electrical nature of a polymeric substrate is an important determinant of interfacial energetics. Many components of mammalian blood, including red blood cells, platelet surfaces, plasma proteins, and morula vascular endothelium, are negatively charged at physiological pH. Thus, ionic groups play an important, but not yet fully understood, role in blood-material interactions.

Sawyer and Pate [Born, *Ann. NY Acad. Sci.*, 201, 4 (1972)] demonstrated that normal vascular endothelium is negatively charged and proposed that the natural blood vessel is thromboresistant due to repulsion between negative charges on the vessel wall and the blood components. Sawyer et al., *Bull. NY Acad. Med.*, 48, 235 (1972) also examined a number of metals and demonstrated that relatively electronegative metals are less thrombogenic than others. One study concluded that polymers with a negative zeta potential, including an acrylic latex combined with a sulfonate detergent, carboxyl cellulose and fluorinated silicones are relatively blood compatible. (Rembaum et al., *Polym. Prepr.*, 16, 191 (1975).

Negative charge by itself, however, is not sufficient to impart thromboresistance to a material. Glass, for example, is a well-known coagulant in spite of its relatively large negative zeta potential. In studies of the blood compatibility of silicone rubber, Musolf et al., *NIH PB*, 90, 666 (1969) found that carboxylation failed to improve the observed blood compatibility. Hageman Factor (an intrinsic blood clotting factor) has been shown to be activated by a variety of negatively charged surfaces. Nossel et al., *Nature*, 221, 74 (1969). Thus, the mechanism of action for a negatively-charged species such as heparin in coagulation inhibition is believed to be much more complex than merely the action of the negative charge.

It is well-known that plasma proteins are rapidly adsorbed when blood contacts an artificial surface, and it is believed that this protein layer influences the thrombogenicity of the surface. For example, the amount of platelet activation appears to be strongly mediated by the adsorbed protein layer. Park et al., *J. Biomed. Mater. Res.*, 20, 589 (1986). The degree of platelet spreading which is promoted by the surface and the adsorbed protein layer is an important parameter for controlling the thrombogenicity of the surface and has been found to affect the relative amounts of proteins which adsorb at the interface. Weathersby et al., *J. Bioeng.*, 1, 395 (1977); Baszkin et al., *J. Biomed. Mater. Res.*, 14, 393 (1980) and Van Dulm et al., *J. Coll. Int. Sci.*, 91, 248 (1983).

More direct investigations of surface charge effects on protein adsorption have been attempted, but conflicting results have been obtained. It has been found, for example, that ionic character in itself has relatively minor effects on protein adsorption when compared to other parameters. Schmitt et al., *J. Coll. Int. Sci.*, 92, 25 (1983); Morrissey et al., *J. Coll. Int. Sci.*, 56, 537 (1976) and Norde et al., *J. Coll. Int. Sci.*, 66, 257 (1978). Van Dulm et al., *J. Coll. Int. Sci.*, 56, 557 (1976) reported that in one case albumin adsorption behavior differed markedly from other situations, and relatively slow initial adsorption rates were observed in the special case where both species were negatively charged.

It has also been demonstrated that polymers with carboxylate functional groups interact with proteins in a different manner than those with sulfonate groups. Bernfeld, P., "Interaction of Polyanions With Blood Components", in *The Amino Sugars*, Balaz E. A. and Jeanloz, R. W. (eds.) Academic Press, New York, 251–256 (1966) and Gelman et al., *Biopolymers*, 12, 541 (1973). Recent work by Fougnot et al., *Biomaterials*, 5, 89 (1984) has shown that the binding of sulphamide and/or sulfonate groups to a substrate produces surfaces with relatively high affinities for albumin, thrombin and antithrombin. These substrates were shown to be relatively blood-compatible when compared to other surfaces.

However, the effect of ionic character on protein adsorption and subsequent thrombogenesis is still quite controversial. Muramatsu et al., *J. Biomed. Mater. Res.*, 17, 959 (1983) studied protein adsorption using static adsorption methods to determine adsorption isotherms on artificial red blood cell surfaces. It was determined that the surface negative charge of the surfaces, as evidenced by the relative number of sulfonic acid groups present, strongly affected the composition, molecular orientation, and/or configuration of adsorbing plasma components. Fibrinogen and gammaglobulin adsorption were particularly affected by surface charge.

The mechanism of heparin action has also been considered in anticoagulation research. Heparin is a naturally-occurring mucopolysaccharide anticoagulant. Its molecular weight ranges from below 10,000 to above 20,000, with the higher molecular weight fraction generally showing a higher level of anti-coagulant activity. Ebert et al., "The Anticoagulant Activity of Derivatized and Immobilized Heparins", in *Biomaterials: Interfacial Phenomena and Applications*, Cooper, S. L. and Peppas, N. A. (eds.), *ACS Adv. in Chem. Services*, 199, 161 (1982). The mechanisms by which heparin exerts its anticoagulant function are not well-defined. Ebert et al., id.; Jozefowicz et al., *Pure and Appl. Chem.*, 56, 1335 (1984) and Olsson et al., *Ann. NY Acad. Sci.*, 416, 525 (1984).

The most potent plasma inhibitor of the coagulation process is antithrombin III (AT-III), which forms inactive stable complexes with serine-proteases including clotting factors IIa, IXa, Xa, IXa and kallikrein. These reactions are believed to be subject to catalysis by heparin and heparin analogs which might be present in some subendothelial or endothelial tissue. The generally accepted scheme is that heparin binds to AT-III and greatly potentiates thrombin binding to AT-III binding sites in the heparin AT-III complex. The complex not only binds to thrombin, but also binds to every active serine protease in the intrinsic coagulation pathway.

Lindsay et al., *Trans. Am. Soc. Artif. Inter. Organs*, 22, 292 (1976) cited a number of conflicting reports on the action of heparin on platelets and concluded that variations in experimental techniques probably account for the many contradictory findings. Their own in vitro platelet retention study indicated that heparin had two antagonistic effects in platelet-foreign surface interactions. First, heparin in the blood was found to act directly on platelets to increase their retention. Second, the reduction of platelet adhesion to surfaces to which heparin was ionically attached led to the conclusion that heparin acted on the foreign surface, probably by competing for cationic sites. This suggests that heparinized surfaces may be passivated, but the heparin may not be performing its normal biological function.

It was found by Gott et al., *Trans. Am. Soc. Artif. Inter. Organs*, 10, 213 (1964) that heparin ionically bound to a polymer surface tends to result in a decreased tendency for the surface to promote coagulation. Since that time, the covalent and ionic binding of heparin and other anticoagulants have been the subject of numerous studies. Jozefowicz et al., id. and Olsson et al., id. review these studies. While ionically bound heparin has demonstrated antithrombogenic characteristics, materials heparinized in this manner have been effective only while they release the ionically bound heparin into the bloodstream. This mechanism is not satisfactory for long-term implantation. Van der Lei et al., *Trans. Am. Soc. Artif. Intern. Organs*, 31, 107 (1985) found that ionically-bound heparin does not increase patency in small diameter polyurethane vascular grafts.

Covalently-bonded heparin surfaces have been developed; and in most, but not all cases [Hashimoto, K., *Tokohu J. Exp. Med.*, 81, 93 (1963)], an improvement in antithrombogenicity of the derivatized surfaces with respect to the untreated surfaces has been shown. In agreement with the foregoing discussion, it has been noted that the surfaces to which heparin is covalently bound tend to activate platelets when exposed to blood or a platelet suspension (Jozefowicz et al., id.). A surface modification of a BIOMER polyurethane vascular graft involving covalently-bound heparin did not result in decreased platelet or fibrinogen deposition in two canine ex vivo experiments. Lelah M.D., Ph.D. Dissertation, Univ. of Wisconsin-Madison (1984).

Recent results by Sharma et al., *ACS Div. Polym. Mat. Sci. Eng. Prepr.*, 53, 423 (1985) indicated that some heparinization methods for polyurethanes resulted in sharply increased fibrinogen adsorption from in vitro competitive adsorption experiments, and also provided a dramatic decrease in platelet adhesion from platelet-rich plasma. These investigators attributed their findings to specific interactions between the platelets and heparin, and did not consider such factors as fibrinogen conformational changes which could result upon adsorption to the different surface.

In any case, the use of covalent heparin binding to achieve an antithrombogenic surface may be of limited use, as exposure to blood is expected to eventually degrade the bound heparin under the action of heparinases.

The development of "heparinoid" materials has generally involved the synthesis of polyelectrolytes with sulfonate and/or carboxylate functionality. Arge, E., *ACTA Med. Scand.*, 155, 496 (1956) and Walker et al., *Biochem. Biophys. Res. Comm.*, 83, 1339 (1978) have hypothesized that the mechanism of heparin action is based on the action of the sulfate and aminosulfate groups on the heparin molecule. Hashimoto, id., also asserted that sulfate or sulfonate groups might simulate the action of a heparinized surface and prevent thrombus formation. Conflicting results were reported by Olsson et al., id., who prepared surfaces of sulfated polysaccharides and found them to be equally "platelet compatible" with heparin in in vitro tests but more thrombogenic than a heparinized surface in a canine arteriovenous shunt.

The previously mentioned study of Muranmatsu et al., id., further confuses the issue since that study demonstrates that an increased concentration of sulfonic acid groups in a polymer leads to a higher amount of platelet adhesion. Jozefowicz et al., id. and Sorm et al., *J. Polym. Sci., Polym. Symp.*, 66, 349 (1979) contend that carboxylic functionality is also essential for heparin-like activity. Sederel et al., *J. Biomed. Mater. Res.*, 15, 819 (1981) synthesized a polyelectrolyte with N-sulfate and carboxylate groups that showed anticoagulant activity in several in vitro trials. Ebert et al., id., found that heparin anticoagulant activity decreased as the degree of carboxylic derivatization increased. Therefore, it appears that the carboxylate and sulfonate functionality play a role in anticoagulant action.

Jozefowicz and coworkers have examined the mechanisms involved in the function of heparinoid materials. In one study, the antithrombotic activity of crosslinked polystyrene was related to the surface density of sulfonate groups. Kanmangne et al., *Biomaterials*, 6, 297 (1985). Other studies involved the preparation and the properties of dextran derivatives, and demonstrated that the anticoagulant activity of these polysaccarrides was due to methylcarboxylic and sulfonated benzylamide groups. Mauzac et al., *Biomaterials*, 3, 221 (1984); Mauzac et al., *Biomaterials*, 5, 301 (1984) and Fisher et al., *Biomaterials*, 6, 198 (1985). These studies have recently been extended by the addition of various amino acid substituents to substituted dextran resins.

Sorm et al., id., prepared a number of synthetic polymers based on poly(methyl methacrylate) and derivatized polymers with sulfate, carboxylate and sulfamide groups in various proportions. The thrombogenicity was determined with an in vitro test of the coagulation time of plasma in the presence of thrombin. It was determined that the highest coagulation activity was found with a copolymer containing a relative amount of 86 percent (of total ionic content) sulfate groups and 14 percent carboxylate groups. The presence or absence of sulfamide groups was not found to have any effect on thrombogenicity.

Helmus et al., *J. Biomed. Mater. Res.*, 18, 165 (1984) examined the role of surface charge of various copolymers of (L-glutamic acid co-L-leucine) and related the surface charge to thrombus formation in implanted vascular grafts in dogs. The initial ionic state controlled the biological interactions. When surface concentrations of non-ionized glutamic acid were less than 10 percent of the maximum, the amount of thrombus formed was a linear function of the degree of ionization. When 10 percent or more of the total surface sites comprised ionized glutamic acid residues, no thrombus was formed, only adhesion of single platelets to the surface was observed. The surface exposed in their canine model showed endothilization upon long blood exposure times, but that event was correlated with the extent of thrombus formation on the surfaces, with the surfaces showing the most extensive thrombus formation also showing the most endothelization.

At present, most ion-containing materials are "model ionic compounds" and do not possess adequate mechanical integrity for biomedical applications. Many of these polymers are hydrogels which must be bonded to a substrate having the necessary properties for the desired application.

As noted above, many types of heparinized polyurethane block copolymers have been tested for blood compatibility, with examples of relatively successful [Heyman et al., *J. Biomed. Mater. Res.*, 19, 419 (1985) and Shibuta et al., *J. Biomed. Mater. Res.*, 20, 971 (1986)] and unsuccessful [Van der Lei, id. and Lelah et al., id.] attempts being reported. Studies of "heparinoid" polyurethanes, however, are less common.

One of the first investigations of polyurethanes was by Rembaum et al., *Biomat. Med. Dev. Art. Org.*, 1, 99 (1973). Polyether polyurethanes containing positive charges in the backbone (cationomers) were synthesized by incorporating a tertiary amine into the hard segment and reacting that group with an alkyl halide. The particular cationic polyurethanes were not studied, but they were reacted with sodium heparin to yield polyurethane-heparin complexes. A chronic carotid artery-jugular vein canine shunt was used to evaluate the thrombogenicity of this complex together with a commercial polyurethane and silicone rubber. While little difference was observed in the rates of platelet deposition on non-heparinized polyurethane or silicone rubber (although the silicone rubber was shown to cause the formation of more emboli), a retardation in platelet deposition was observed for the polyurethane-heparin complex.

Ito et al., *J. Biomed. Mater. Res.*, 20, 1157 (1986) examined anionic polyurethanes with carboxylic acid functionality. The anionic polyurethane selectively adsorbed albumin, did not cause a conformational change of plasma proteins adsorbed and suppressed the adherence and deformation of platelets, but did not deactivate the clotting system. Thus, the polyurethane was considered moderately thrombogenic. A heparin-bound derivative of this anionic polyurethane was not favorable for albumin adsorption, caused plasma protein denaturation and induced platelet adherence and activation, but did not activate the clotting system (as measured by thrombin times). The question of "biocompatibility" is not yet resolved for these materials, as one would presume that neither platelet activation nor activation of the clotting system would be desirable.

Two separate studies by Cooper and coworkers [Lelah et al., *J. Biomed. Mater. Res.*, 18, 475 (1984) and Lelah et al., "Blood Compatibility of Polyethylene and Oxidized Polyethylene in a Canine Ex Vivo Shunt: Relationship to Surface Properties," in *Polymers as Biomaterials*, Shalaby et al (eds.) Plenum Press, New York, 257—277 (1984)] demonstrated that ionization of polyurethanes is a useful technique for improving blood compatibility.

In the first study, two uncharged polyurethanes based on 21.5 and 38 weight percent methylene bis(p-phenyl isocyanate) (MDI), N-methyldiethanolamine (MDEA), and poly(tetramethylene oxide) (PTMO) having a number average molecular weight of about 1000 were examined using the canine ex vivo series shunt technique. Also studied were the sulfonate-containing zwitterionic, neutralized anionic, and quaterinized cationic derivatives of the MDEA-chain-extended base material containing 38 weight percent MDI.

The platelet deposition profiles of the polyurethane zwitterionomer and anionomer were more thromboresistant than the uncharged polyurethane, while the polyurethane cationomer was the most thrombogenic material of the series. The thromboresistance of the zwitterionomer correlated with a high concentration of the mobile side chain ionic sulfonate group at the surface. Ionic mobility at the interface appeared to strongly influence the blood response to these materials.

Platelet deposition profiles from a second study showed that for a non-ionized polyurethane containing 24 weight percent MDI and the analogous zwitterionomer, zwitterionization was found to improve the thromboresistance of a non-ionized material. The exact mechanisms of this action, however, were not investigated.

The base polymer utilized in the second study (in place of the MDEA-chain-extended system) was based on MDI, PTMO having a number average molecular weight of about 1000, and 1,4-butanediol (BD). The use of butanediol as a chain extender provides a base material with superior physical properties to those observed with an analogous polymer chain-extended with MDEA. This is attributed to the superior ability of the hard segments in the BD-chain extended system to aggregate and crystallize. Lelah et al., *Polyurethanes in Medicine*, CRC Press, Boca Raton, Fla. (1986). Butanediol is often used in commercial products, and BD is the chain extender used in PELLETHANE polyurethanes (Lelah et al., id.) and in DESERET VIALON polyurethanes.

Therefore, in spite of many prior art disclosures in the area of biocompatible materials, a need still exists for improved polymeric materials that are more suitable for blood-contacting applications, and which possess the desired bulk physical and surface properties.

SUMMARY OF THE INVENTION

The present invention relates to polyurethane block copolymers that include particular polar functional groups and biocompatible devices prepared therefrom.

The copolymers can include a mole ratio of about 1.5/0.5/1.0 to about 10/9/1 of an organic diisocyanate, a $C_2$-$C_{14}$ alkyl or aryl or diamine and a polyol having a number average molecular weight from about 500 to about 3000. In one preferred embodiment, the copolymer includes a 3/2/1 mole ratio of an organic diisocyanate, a $C_2$-$C_{14}$ alkyl or aryl diol or diamine and a polyol having a number average molecular weight from about 500 to about 2000, more preferably about 1000.

These copolymers are further modified via a bimolecular nucleophilic substitution reaction wherein up to about 25 percent of the urethane hydrogen atoms, and preferably between about 10 and 15 percent of the urethane hydrogen atoms, are replaced with a combination of lower alkyl ($C_1$-$C_6$) straight chain or branched sulfonate groups and lower alkyl ($C_1$-$C_6$) straight chain or branched carboxylate groups.

The organic diisocyanate can include 2,4-toluene diisocyanate, 2,6-toluene diisocyanate, methylene bis(p-phenyl isocyanate), 1,5-naphthalene diisocyanate, methylene bis(p-cyclohexyl isocyanate), 1,6-hexane diisocyanate, isophorone diisocyanate and cyclohexyl diisocyanate.

The diol or diamine can include 1,4-butanediol, ethylene diamine, 4,4'-methylene bis(2-chloroaniline), ethylene glycol and hexanediol. The diol and diamine can comprise a blend of two or more reactive species, preferably having similar reactivities. In addition, a hydroxy-functional amine such as a radical represented by the formula $(HOR)_2NR_1SO_3H$ can be used in place of or in addition to the diol or diamine. In the above formula R and $R_1$ can be independently selected from lower alkyl ($C_1$-$C_6$) groups. Moreover, the sulfonate group can be replaced with a carboxylate group.

The polyol can include polyethylene oxide, polypropylene oxide, polytetramethylene oxide, polyisobutylene, polybutadiene, polyethylene adipate, polytetramethylene adipate, polycaprolactone and polydimethylsiloxane. The polyol can also comprise a blend of two or more species, preferably having similar reactivities.

It is particularly preferred to use an equimolar ratio (to within about 5 percent) of the isocyanate to the other active hydrogen atoms in the copolymer mixture such as the hydroxyl and amine functional groups.

The present invention also relates to a method of producing the copolymers described herein and medical devices formed with the copolymers of this invention. Such devices are useful in applications where a biocompatible material is needed to avoid or minimize adverse reactions upon contact with blood or tissue.

The copolymer may comprise all of the device or only the surface which will be in contact with the body fluids. In particular, these materials may be used as vascular prostheses in the venous or arterial system, as heart patches or as heart valves, as the outer encapsulant of implantable devices such as heart pacemakers, and as catheters or the outer sheath of catheters in contact with body fluids and the like. They may also be used as temporary coverings for skin loss resulting from either mechanical damage or burns, or they may be used as a covering for open wounds. Additionally these devices may be used as channels through which body fluids may be passed in the heart-lung and kidney machines, for example. Indeed, the materials of these devices generally have the properties of semipermeable membranes and may be used as such in extracorporeal devices.

Thus the present copolymers are biocompatible, and exhibit improved physical strength and hydrophilic properties. For example, in blood-contacting applications in which medical devices (catheters, access shunts, implants and the like) are fabricated from these polymers, platelet deposition decreases and platelet spreading and activation is substantially lessened. Surface analysis of these polymers indicates that, depending on the contacting environment, a rearrangement may take place to minimize interfacial tension. Fibrinogen deposition on the surfaces of these polymers is higher, which indicates a particular fibrinogen-surface interaction during platelet contact.

In a particularly preferred embodiment, the polyurethane block copolymers of this invention comprise the reaction product of a 3/2/1 mole ratio of methylene bis(p-phenyl isocyanate) (MDI), 1,4-butanediol (BD) and polytetramethylene oxide (PTMO) having a number average molecular weight of about 1000, respectively, which reaction product is further modified in a post-synthesis alkylation step to include from about 5 to 25 weight percent of propyl sulfonate and propyl carboxylate groups based on the total weight of the copolymer.

Numerous other advantages and features of the present invention will become more readily apparent to those skilled in the art based on the following detailed description of the invention, the accompanying examples and drawings and the appended claims.

DETAILED DESCRIPTION OF THE INVENTION

Figure 1:
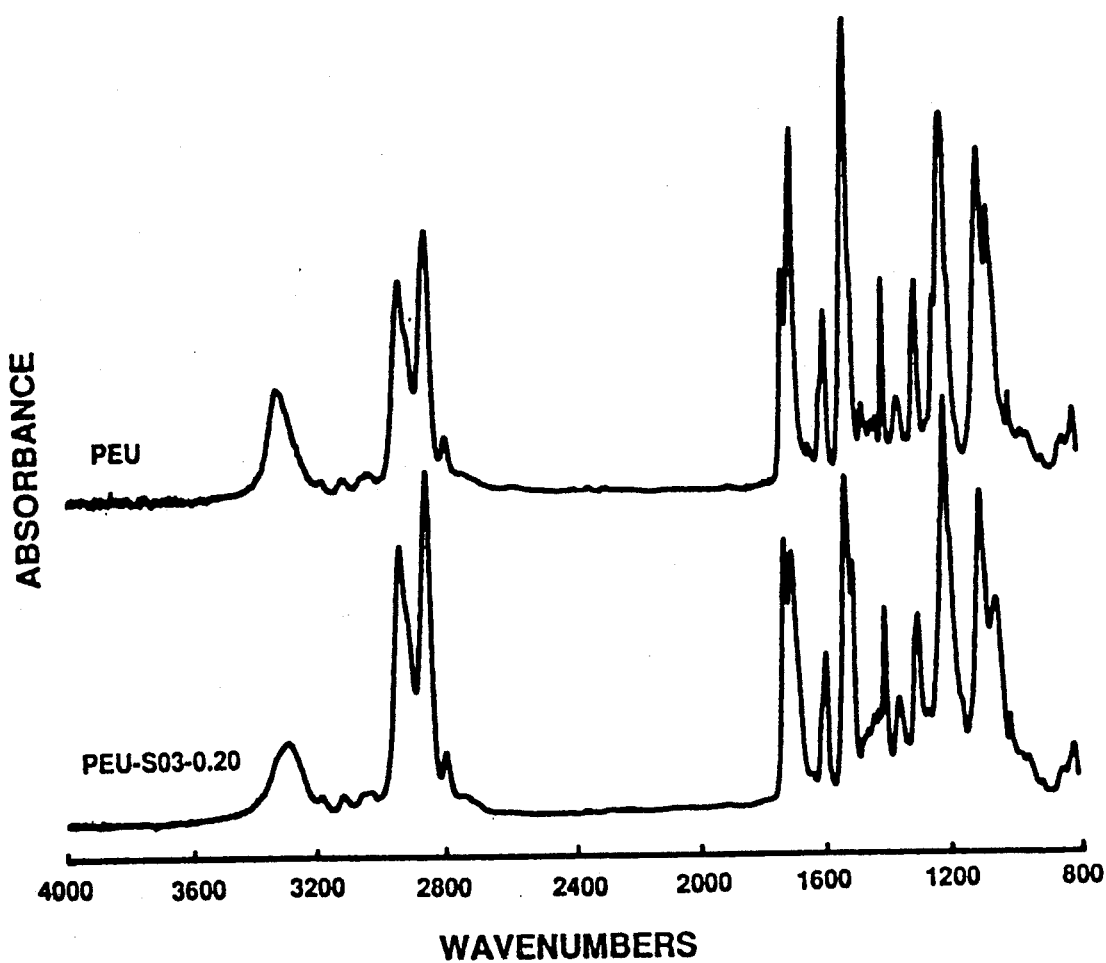
FIG. 1 illustrates infrared absorption spectra for a polyurethane and a polyurethane ionomer having about twenty percent of the urethane hydrogen atoms replaced with propyl sulfonate groups.

For purposes of illustrating the present invention and the practice thereof, the method of preparing the present polyurethane block copolymers and the preparation of certain chemical intermediates is described with reference to particular examples of copolymers and testing procedures for determining bulk and surface characteristics, and the biocompatibility of the copolymers. It will be understood, however, that the copolymers of this invention are not limited only to those materials specifically described herein.

In accordance with the present invention, modifications to the polymer chain are performed, and bulk characterization techniques are utilized for the analysis of properties such as microphase separation. Bulk properties are related to surface properties, and the resulting polyurethane ionomers are evaluated for blood compatibility through a canine ex vivo blood-contacting experimental procedure. Although bulk modifications are performed, it should be recognized that the present polymer compositions can readily be used for coatings, or can be adapted for use as surface modifying agents.

I. MATERIALS AND METHODS

A polyether-polyurethane (PEU) based on methylene bis(p-phenyl isocyanate) (MDI), 1,4-butanediol (BD) and a polytetramethylene oxide (PTMO) having a number average molecular weight of about 1000 is first synthesized in a 3/2/1 mole ratio. The chemical structures of the starting materials shown below:

| methylene bis(p-phenyl isocyanate) | (MDI) |
|---|---|
| OCN-C$_6$H$_4$-CH$_2$-C$_6$H$_4$-NCO | |
| 1,4-butanediol | (BD) |
| HO-CH$_2$CH$_2$CH$_2$CH$_2$-OH | |
| polytetramethylene oxide, 1000 MW | (PTMO) |
| HO-(CH$_2$CH$_2$CH$_2$CH$_2$O)$_n$H | |

A grafting reaction procedure is performed employing a bimolecular nucleophilic displacement reaction of the urethane hydrogen atoms. The urethane nitrogens are first reduced by reaction with sodium hydride in a solvent such as N,N-dimethylacetamide (DMA) which results in the production of hydrogen gas. This reaction is followed by reaction with 1,3-propane sultone which reacts with the nitrogen anion to produce a derivatized urethane linkage. The extent of sulfonate substitution is systematically varied from about 5 to about 20 percent replacement of the urethane hydrogen atoms.

The sodium salt of 4-iodobutanoic acid (Aldrich Chemical Co., Milwaukee, Wis.) can be used instead of propane sultone for polymers having twenty percent of the urethane hydrogen atoms replaced. The synthetic procedure in this instance is essentially the same, except that a mixed solvent of DMA and dimethyl sulfoxide (DMSO) (in a 3:1 ratio by volume) is used because of the limited solubility of iodopropionic acid in DMA.

A. Sample Preparation

After synthesis, the modified copolymers are extracted for about 48 hours with toluene in a Soxhlet extractor to remove contaminants, oligomeric materials and any residual propane sultone that may be present. After briefly drying under vacuum to remove residual toluene, the resulting copolymers are dissolved in DMA and then cast into Teflon pans for bulk property testing or are coated into the inner lumen of chromic acidoxidized polyethylene tubing for surface property and blood compatibility evaluation. In both casting procedures, cast films are first dried under a nitrogen stream (in the case of tubing) or in a 70 degree C forced-air oven (for bulk sheets) for at least 48 hours to remove most of the DMA. The final drying stage involves drying the coated tube or sheet under vacuum at 60 degrees C for at least 48 hours to remove any residual DMA.

Typically, polyurethane elastomers comprise rigid and flexible alternating segments. The hard (rigid) segment consists of a diisocyanate that has been chain extended with a low molecular weight diol or diamine. The soft (flexible) segment is a long chain macroglycol with a number average molecular weight between about 500 and 5000.

Preferred isocyanates for use in the practice of the present invention include 2,4-toluene diisocyanate, 2,6-toluene diisocyanante, methylene bis (p-phenyl isocyanate), 1,5-naphthalene diisocyanate, methylene bis(p-cyclohexyl isocyanate), 1,6-hexane diisocyanate, isophorone diisocyanante and cyclohexyl diisocyanante.

Preferred chain extenders include 1,4-butanediol, ethylene diamine, 4,4-methylene bis(2-chloroaniline), ethylene glycol and hexanediol.

Preferred polyols include polyethylene oxide, polypropylene oxide, polytetramethylene oxide, polyisobutylene, polybutadiene, polyethylene adipate, polytetramethylene adipate, polycaprolactone and polydimethylsiloxane.

B. Sample Nomenclature

A list of the particular copolymers prepared and the nomenclature used herein is shown in Table I.

TABLE I

| | SAMPLE DESIGNATIONS | | |
|---|---|---|---|
| | Percent of Urethane Hydrogens Replaced | | |
| Polymer | Total Percent Replaced | Percent Replaced Using Propane Sultone | Percent Replaced Using Iodo-Butyric Acid Salt |
| PEU | 0 | 0 | 0 |
| PEU-SO3-0.05 | 5 | 5 | 0 |
| PEU-SO3-0.10 | 10 | 10 | 0 |
| PEU-SO3-0.15 | 15 | 15 | 0 |
| PEU-SO3-0.20 | 20 | 20 | 0 |

TABLE I-continued

| | SAMPLE DESIGNATIONS | | |
|---|---|---|---|
| | Percent of Urethane Hydrogens Replaced | | |
| Polymer | Total Percent Replaced | Percent Replaced Using Propane Sultone | Percent Replaced Using Iodo-Butyric Acid Salt |
| SO3-0.15 COO-0.05 | 20 | 15 | 5 |
| SO3-0.10 COO-0.10 | 20 | 10 | 10 |

As indicated in TABLE I, the control non-ionized polyurethane is referred to as PEU. Sulfonate incorporation is denoted by SO3 to distinguish those materials from materials prepared by grafting long alkyl chains to the base PEU polymer. The fraction of urethane hydrogens substituted is indicated by the final portion of the sample designation. Thus, PEU-SO3-0.20 has a twenty percent displacement of urethane hydrogen atoms with propyl sulfonate groups. Polyurethanes having both sulfonate and carboxylate functionality are not identified herein with the PEU designation; but are identified, for example, with the designation SO3-0.15 COO-0.05, which indicates fifteen percent displacement of urethane hydrogen atoms with propyl sulfonate groups and five percent displacement of urethane hydrogen atoms with propyl carboxylate groups. See TABLE II.

C. Bulk Property Characterization

Differential scanning calorimetry (DSC) thermograms are recorded from −150 degrees C. to 230 degrees C. using a Perkin-Elmer DSC-2 equipped with a data-processing unit that subtracts background readings and normalizes sample thermograms for sample weight. The heating rate is 20 degrees C./min for the initial heating up to 200 degrees C. Samples are quench-cooled to −130 degrees C. at 320 degrees C./min and then reheated at a rate of 20 degrees C./min.

Transmission infrared spectroscopy is performed with a Nicolet 7199 FTIR operating at a resolution of 2 reciprocal centimeters ($cm^{-1}$). Dynamic mechanical analysis is accomplished with a microprocessor-controlled Rheovibron DDV-II. Samples are cooled to −150 degrees C., and data are taken at a test frequency of 110 Hz and a temperature rise rate of 2 degrees C/min until sample failure. Room temperature uniaxial stress-strain data are taken on an Instron table model tensile testing device at a crosshead speed of 0.5 inch/min (57 percent/min.). Samples are prepared using an ASTM 1708 standard die.

D. Surface Property Determination

Surface properties are determined directly on a coated polyethylene surface prior to exposure to blood. Random sections of a coated polyurethane tube are selected for the various methods of analysis. The contact angle data from the numerous sections tested indicate that the coatings are consistent and uniform in all sections of tubing for each material tested.

ESCA data are collected using a Surface Science Laboratories SSX-100 ESCA spectrometer using an AlK$_{alpha}$ x-ray source. The characteristics of this instrument have been described by Yoon et al., *Macromolecules*, 19, 1968 (1986), and the same instrument operating under the same conditions has been used to characterize the surface structure of the present polyurethane copolymers. The circular spot size irradiated with monochromatic x-rays is 600 micrometers in diameter. Surface charging which occurs as a result of the non-conductive surfaces is neutralized with an electron flood gun. High resolution C1 s spectra are obtained using a 25 eV pass energy, and spectra for the determination of elemental percentages are obtained for all elements present at a 100 eV pass energy. A 30 degree solid-angle electron collection aperture is used in the electron lens system, and all spectra are collected at a single take-off angle of 55 degrees. All ESCA data are processed using the software provided with the instrument. The C1 s core level spectra of the polymers can be resolved with reference to known binding energy data for nitrogen-substituted polymers or model compounds using the assumption of Gaussian peak shapes.

Attenuated total reflectance (ATR) infrared spectroscopy is performed using a Nicolet 7199 FTIR, coupled with a Barnes 300 ATR accessory and 45 degree germanium crystal coated tubings are sliced and pressed against the crystal. Spectra are collected at a resolution of 2 $cm^{-1}$.

Underwater contact angle measurements are made using the captive bubble technique of Hamilton, *J. Colloid Interface Sci.*, 40, 219 (1972), modified for use on curved inner tubing surfaces. At least twelve separate measurements are performed on at least five different, randomly selected tubing sections of each material. Each surface is allowed to equilibrate under double-distilled water overnight. Surface-air-water and surface-octane-water static bubble contact angles are measured. When possible, polar and dispersive components of the surface energy and the surface-water interfacial energy are calculated using harmonic mean and geometric mean approximation methods. Advancing and receding contact angles of water on polymer-coated tubings are measured using methods well known to those skilled in the art. All measured contact angles are reported as the angles through the water phase.

E. Blood Compatibility Evaluation

A study using a canine ex vivo series shunt is used to evaluate the blood compatibility of these polyurethane block copolymers. Blood exposure times range from 1 to 60 minutes. Each material is examined in three separate random segments in each shunt. A control surface of INTRAMEDIC polyethylene can be examined in each shunt, if NIH Standard Reference Polyethylene is not available in the necessary inner diameter.

The animal studies were performed as described in Lelah et al., *J. Biomed. Mater. Res.*, 18, 475 (1984) which is incorporated herein by reference. Initial flow rates are carefully controlled using a clamp (downstream from the test sections) to average levels of 300 m/min (±5 percent) which corresponds to an average wall shear rate of about 1600 $sec^{-1}$.

Samples prepared for scanning electron microscopy are viewed using a JEOL-JSM 35C at a 12 kV accelerating voltage.

II. RESULTS AND DISCUSSION

A. Infrared Spectroscopy

FIG. 1 shows the infrared survey spectra for PEU and an ionomer designated PEU-SO3-0.20. The absorption band of the —NH bond at 3340 $cm^{-1}$ was clearly reduced in intensity following substitution.

The other important difference in the spectra of FIG. 1 is in the carbonyl band between 1650 and 1750 $cm^{-1}$. In the non-ionized PEU polymer, the carbonyl absorption is found at 1730 $cm^{-1}$ this represents "free" carbonyl groups that do not hydrogen bond with urethane NH groups; and to a larger extent at 1700 $cm^{-1}$, hydrogen-bonded carbonyl groups. While the urethane carbonyl groups were primarily hydrogen-bonded in the PEU base material, the relative fraction of free carbonyl groups was much greater in PEU-SO3-0.20 than in PEU. Similar results observed in sulfonated polyurethane systems can be attributed to the possibility that the urethane groups bind to the stronger proton-accepting sulfonyl groups instead of to the carbonyl group. Another explanation for the increase in free carbonyl upon ionization is that there is a disruption of ordered hard segment packing arrangements upon ionization.

The first column of Table II includes numerical comparisons of the "nonbonded" to "bonded" urethane carbonyl ratio in the bulk, and it can be seen that the proportion of nonbonded carbonyl groups goes through a maximum as the level of ionization is increased. The relative similarity between the spectra of polymers PEU-SO3-0.20, SO3-0.15 COO-0.05, and SO3-0.10 COO-0.10 indicates that the hard segment ordering is primarily a function of the percentage of urethane hydrogen substitution.

TABLE II

INFRARED SPECTROSCOPIC ANALYSIS OF POLYURETHANE ANIONOMERS

| Polymer | "Nonbonded" to "Bonded" Urethane Carbonyl Absorbance Ratio[a] | | "Hard" to "Soft" Segment Absorbance Ratio[b] | |
|---|---|---|---|---|
| | Bulk | ATR | Bulk | ATR |
| PEU | 0.57 | 0.55 | 0.49 | 0.36 |
| PEU-SO3-0.05 | 0.83 | 0.72 | 0.50 | 0.39 |
| PEU-SO3-0.10 | 1.09 | 0.75 | 0.48 | 0.35 |
| PEU-SO3-0.15 | 1.14 | 0.78 | 0.48 | 0.38 |
| PEU-SO3-0.20 | 1.05 | 0.98 | 0.48 | 0.39 |
| SO3-0.15 COO-0.05 | 1.07 | 1.00 | 0.50 | 0.40 |
| SO3-0.10 COO-0.10 | 0.99 | 0.98 | 0.48 | 0.40 |

[a] $A(1702\ cm^{-1})/A(1732\ cm^{-1})$
[b] $A(1597\ cm^{-1})/A(1111\ cm^{-1})$

The "hard-to-soft" segment absorbance ratio, or the ratio of absorbance at 1597 cm$^{-1}$ (which is characteristic of the benzene ring in the hard segment) and at 1111 cm$^{-1}$ (which is characteristic of the polyether in the soft segment) shows little variation in the bulk infrared spectra. This result is expected because the chemical changes in the bulk to these polymers are not significant.

B. Thermal Analysis

Figure 2:
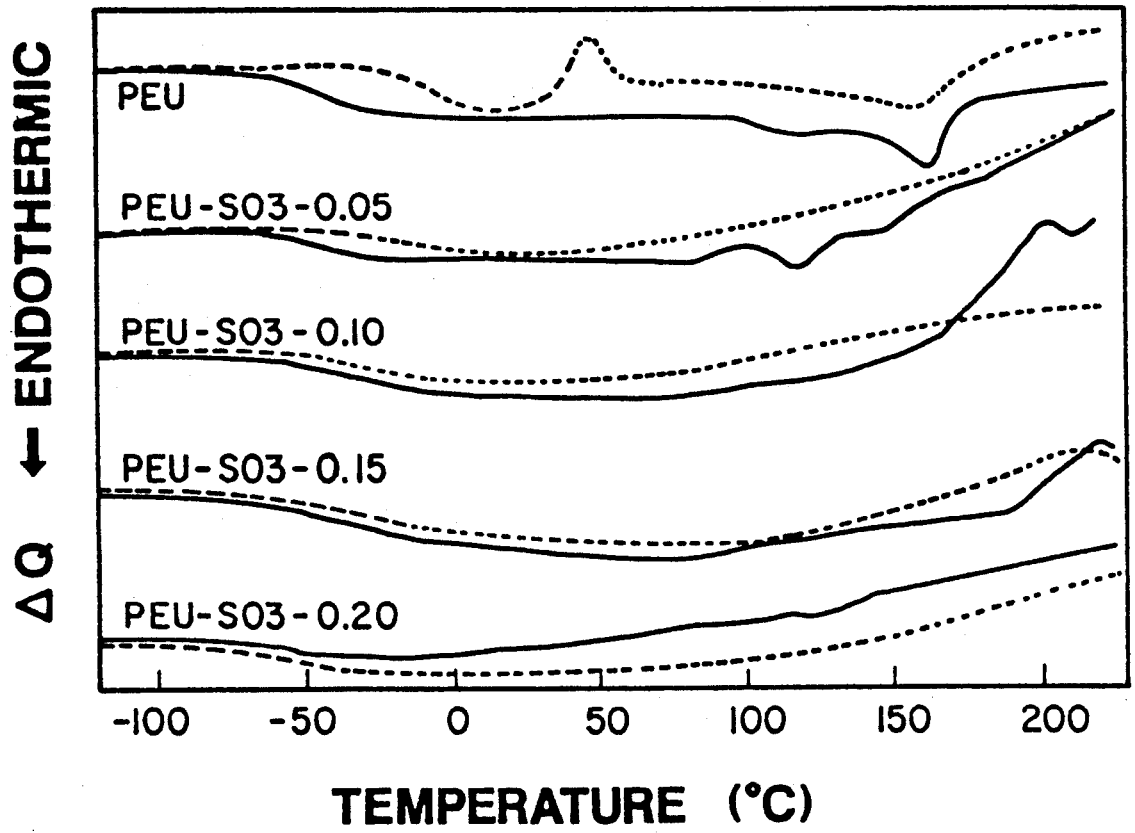
FIG. 2 illustrates differential scanning calorimetry (DSC) curves for sulfonated polyurethanes.
Figure 5:
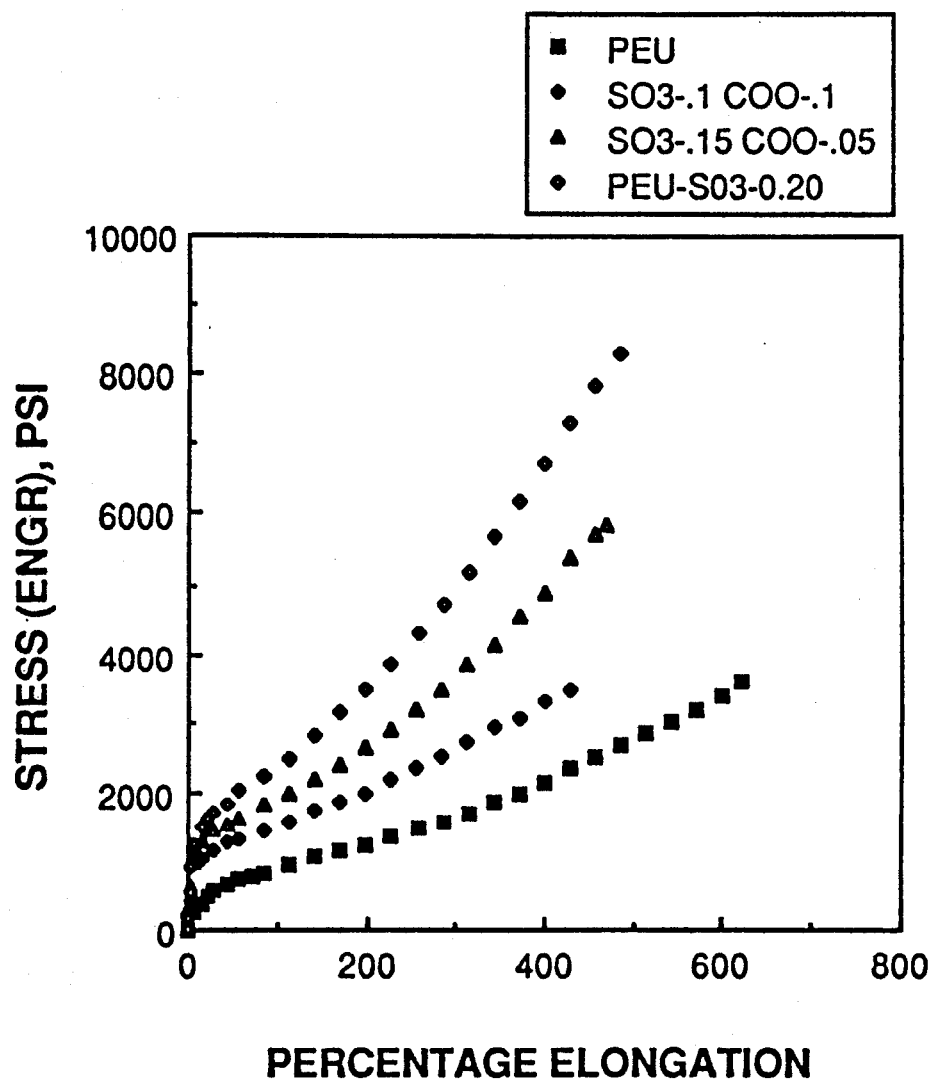
FIG. 5 illustrates the stress-strain curves for a non-ionized polyurethane and for ionomers having both sulfonate and carboxylate functionality.

DSC curves are shown in FIG. 2 for the sulfonated polyurethanes, and the thermal analysis data are summarized in Table III. For each copolymer, FIG. 5 shows the DSC curves for the initial heating at 20 C/min of the as-cast sample (solid lines) and after reheating of the sample at a rate of 20 degrees C/min (dotted lines) and quench-cooling at −320 degrees C/min. The data are consistent with prior art thermal studies of similar polyurethane anionomers.

Initially, there is no significant change in the glass transition temperature (Tg) of the soft segment, but increasing the degree of ionization to the levels of PEU-SO3-0.10 and PEU-SO3-0.15 produces materials with a high soft segment Tg which indicates a decrease in the degree of phase separation with ionization. As noted in the foregoing discussion of the infrared spectroscopic data, this increase in Tg is probably the result of a disruption of hard segment ordering and an increased solubilization of hard segments in the soft segment phase.

Further ionization for copolymer PEU-SO3-0.20 causes the soft segment Tg to become about equal to that of the unmodified PEU. This indicates an increase in phase separation which is consistent with the infrared observations where a decrease in nonbonded urethane hydrogen was observed at the highest ionization level. The increase in the hard/soft segment polarity difference upon ionization is the probable driving force for increased phase separation, and this polarity difference appears to overcome the unfavorable hard segment packing arrangements.

An endotherm at high temperature was observed for PEU, as shown in FIG. 2. In the absence of high-temperature annealing, endotherms occurring at temperatures over 100 degrees C are associated with long-range order in the hard segment. The disappearance of high-temperature endotherms upon ionization confirm that hard segment ordering is less in ionized polyurethanes than in PEU.

When PEU is quenched from a high temperature, a relatively phase-mixed state is "frozen" in, resulting in a relatively high soft segment glass transition temperature when the material is reheated. As shown in FIG. 2, the magnitude of this Tg shift upon quenching is greatest for the relatively well-phase-separated PEU material and decreases upon ionization. The phase separated PEU-SO3-0.20, however, does not exhibit this Tg shift.

Table III shows that the polyurethane anionomers with both sulfonate and carboxylate groups are quite similar to PEU-SO3-0.20, and all DSC curves of these carboxylated systems are nearly indistinguishable from the completely sulfonated PEU-SO3-0.20.

TABLE III

Thermal Analysis Data for Polyurethane Anionomers

| | Glass Transition Temperature, C. | | | |
|---|---|---|---|---|
| | for initial heating: | | for heating after quench: | |
| Polymer | Midpoint | Onset | Midpoint | Onset |
| PEU | −44 | −60 | −30 | −47 |
| PEU-SO3-0.05 | −45 | −62 | −24 | −53 |
| PEU-SO3-0.10 | −35 | −62 | −28 | −53 |
| PEU-SO3-0.15 | −36 | −62 | −36 | −61 |
| PEU-SO3-0.20 | −46 | −70 | −44 | −70 |
| SO3-0.15 COO-0.05 | −47 | −71 | −44 | −70 |
| SO3-0.10 COO-0.10 | −45 | −71 | −44 | −70 |

This similarity indicates a likeness in bulk morphologies between these materials, and indicates that the polymer physical properties are more a function of the percentage of urethane hydrogen displacement than of the type of ionic functionality that is present.

C. Dynamic Mechanical Analysis

Figure 3:
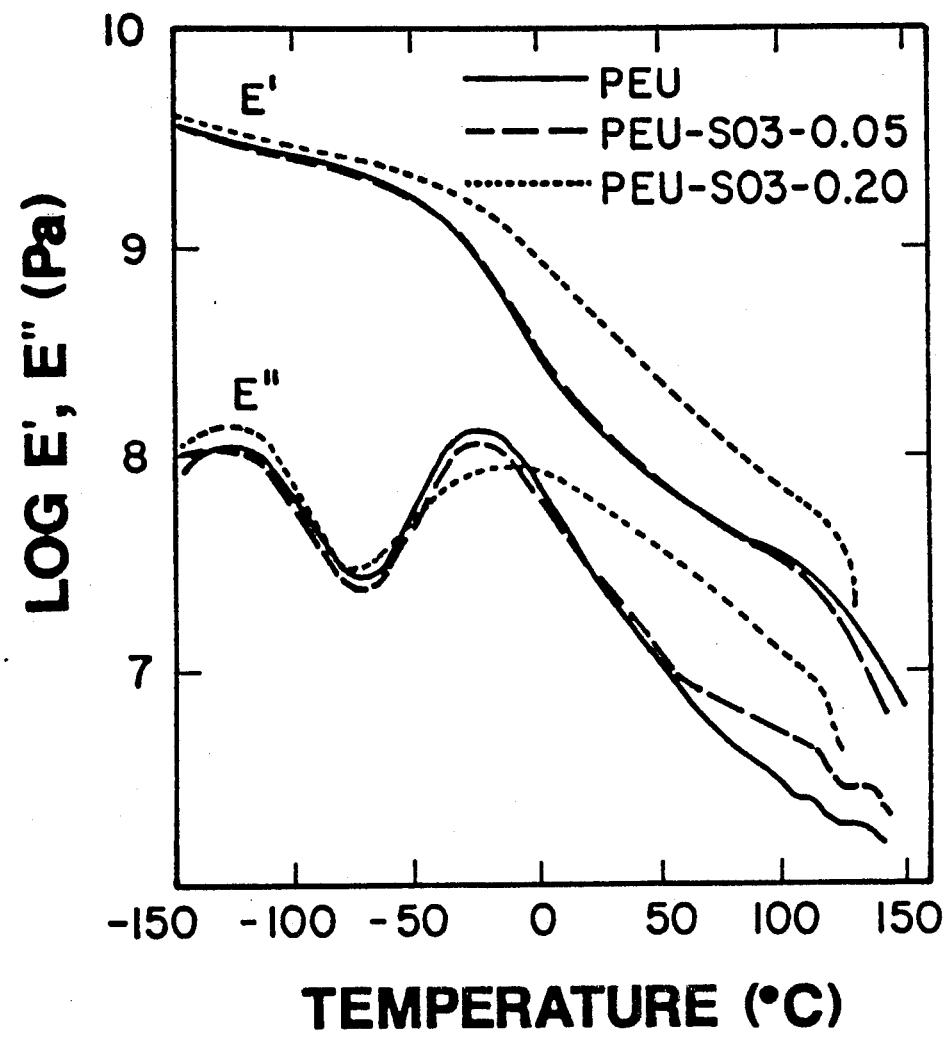
FIG. 3 illustrates the results of dynamic mechanical analysis for a non-ionized polyurethane and for polyurethanes with low and high levels of ionization.

The results of dynamic mechanical analysis for the non-ionized PEU, and for low and high levels of ionization, are presented in FIG. 3. These results are consistent with the DSC data. A significantly higher plateau modulus is observed in PEU-SO3-0.20, which can be attributed to the regaining of a high degree of phase separation along with an enhanced domain cohesion due to the high ionic content. Dynamic mechanical behavior for SO3-0.15 COO-0.05 and SO3-0.10 COO-0.10 is similar to that of PEU-SO3-0.20, which is expected considering the similarity of results of the other bulk characterization methods.

Figure 6:
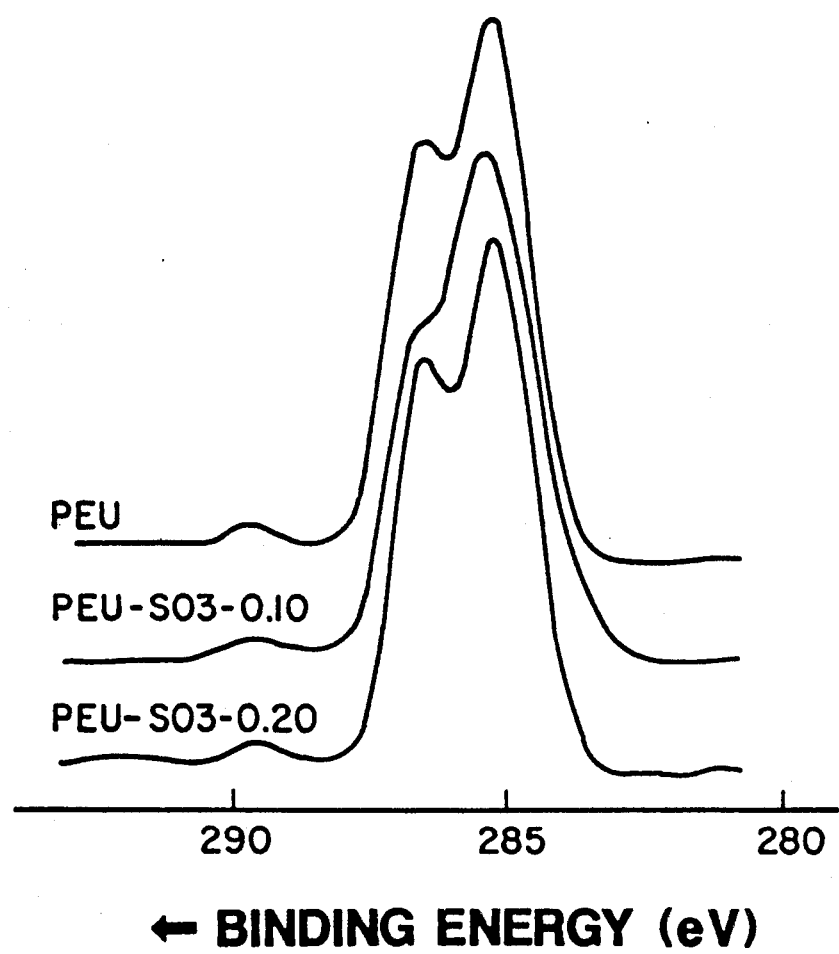
FIG. 6 illustrates the $C_{1S}$ high resolution ESCA spectra for a non-ionized polyurethane and for ionomers having sulfonate functionality.

A high temperature transition, not detected by DSC and believed to be a hard segment glass transition, has been detected for these polymer systems in prior art disclosures, and may be indicated in FIG. 6 for PEU-SO3-0.20. Heating past this transition results in a dimensional stability even lower than that observed for the non-ionized PEU. This drop in the storage modulus at high temperature reduces the high-temperature utility of these ionized materials.

D. Tensile Properties

Figure 4:
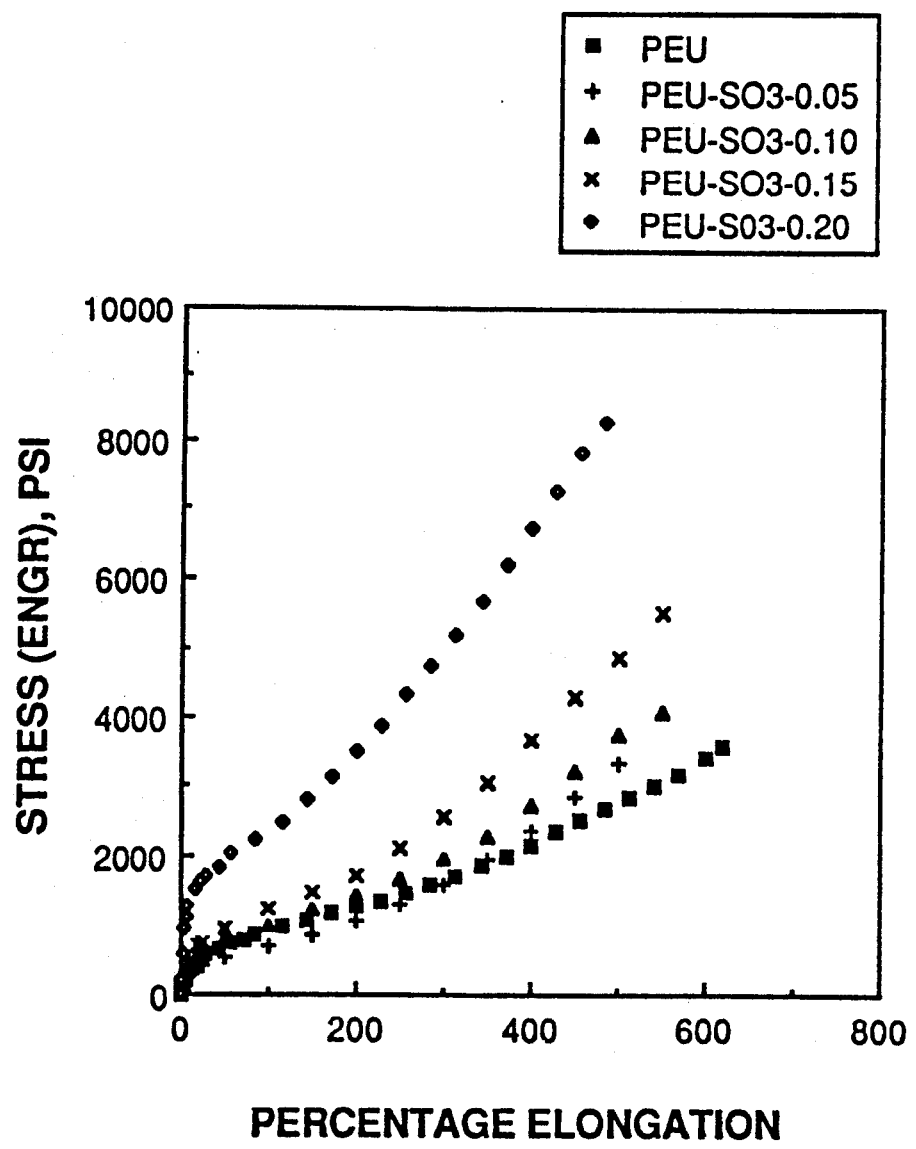
FIG. 4 illustrates the stress-strain curves for a non-ionized polyurethane and for certain sulfonated polyurethane ionomers.

Stress-strain data are summarized in Table IV, and stress-strain curves are shown in FIGS. 4 and 5. The tensile behavior of these materials is consistent with prior art disclosures for polyurethane ionomers. Low levels of ionization render greater ultimate properties but tend to decrease the modulus. This observation is consistent with the dynamic mechanical data in which little change in the E' was seen at low ionization levels. A sudden jump in the modulus was observed as the highest level of ionization was reached.

All of the materials containing a total of twenty percent substitution of the urethane hydrogen atoms possessed a significantly higher Young's modulus than the other polyurethanes studied. However, as shown in Table IV and in FIG. 5, replacing some of the sulfonate groups with carboxylate functionality substantially decreased both percentage elongation and stress at failure.

tion of ionic content, ranging from 2 percent for the base polymer PEU to 150 percent for PEU-SO3-0.15. While the problem of hydration may have to be accounted for in the use of these materials for applications requiring equilibration with the atmosphere, the use of these polymers as coatings onto substrata for blood-contacting applications is not precluded.

E. Surface Properties: Attenuated Total Reflectance Infrared (ATR) Spectroscopy Because of the relatively deep penetration of this technique (1000–10,000 A), good agreement of trends in transmission and total reflectance infrared spectroscopy would be expected. While numerical results for transmission infrared spectroscopy and bulk infrared spectroscopy cannot be directly compared, the trends in the transmission and reflectance spectra although not identical, provide some information about the surface chemical composition relative to that of the bulk.

Table II shows that as the degree of sulfonation increased, the relative ratio of nonbonded-to-bonded urethane carbonyl groups passes through a maximum in the

TABLE IV

Physical Properties for Polyurethane Anionomers

| Polymer | Young's Modulus PSI | Young's Modulus MPa | Ultimate Stress PSI | Ultimate Stress MPa | Percent Elongation at Failure | Percent (of original weight) water absorbed after 48 hrs. at room temperature: after exposure to air (50 percent humidity) | after immersion in water |
|---|---|---|---|---|---|---|---|
| PEU | 4400 | 30 | 3600 | 25 | 620 | 0.28 | 2.2 |
| PEU-SO3-0.05 | 3900 | 27 | 3400 | 23 | 500 | 0.28 | 4.3 |
| PEU-SO3-0.10 | 4200 | 29 | 4100 | 28 | 550 | 0.41 | 31.0 |
| PEU-SO3-0.15 | 4500 | 31 | 5500 | 38 | 540 | 0.50 | 150 |
| PEU-SO3-0.20 | 21500 | 148 | 8300 | 57 | 480 | 0.56 | >1000 |
| SO3-0.15 COO-0.05 | 18000 | 124 | 5710 | 39 | 450 | ND | ND |
| SO3-0.10 COO-0.10 | 15000 | 103 | 3400 | 23 | 420 | ND | ND |

ND = Not Determined

This observation and the decrease in Young's modulus with an increase in the proportion of carboxylate substitution suggest that the hard segment domain cohesion decreases with the level of carboxylate incorporation into the copolymer. The carboxylate substitution still affected the polymer properties, however, because the modulus and stress at failure were higher for SO3-0.10 COO-0.10 than for the PEU-SO3-0.10. Similarly, SO3-0.15 COO-0.05 had a higher modulus and stress at failure than PEU-SO3-0.15.

The ionized materials were found to be somewhat water-sensitive to the point that the tensile properties were significantly affected by exposure to the atmosphere. Water absorption results are shown in TABLE IV for polymer samples stamped out of an ASTM 1708 die and either equilibrated for 48 hours in air at room temperature and 50 percent relative humidity or placed underwater for 48 hours. The largest drop in properties was observed for PEU-SO3-0.2. A sheet of this material that was exposed to the atmosphere as described above showed a drop in Young's modulus to 80 MPa, a drop in ultimate tensile strength to 31 MPa, and decrease in elongation at break to nearly 300 percent, in spite of having measured weight gain well below 1 percent. Hwang et al., J. Macromol. Sci. Phys., B23, 153–174 (1984) noted that similar polymers with ionic contents corresponding to urethante hydrogen replacement levels of over 22 percent absorbed water from the atmosphere and were rendered insoluble in DMA. As indicated in Table IV, when PEU-SO3-0.2 was soaked in water overnight, a polymer-water hydrogel formed weighing over ten times more than the base polymer. Water uptake under these conditions was a strong function bulk. The ATR spectra for the moderately ionized materials (PEU-SO3-0.05, PEU-SO3-0.10 and PEU-SO3-0.15) were quite similar. Moreover, the ratio of nonbonded-to-bonded urethane carbonyl groups did not pass through a maximum with increasing ionic content, as was observed in the bulk polymers of this series. One explanation of this occurrence is that in materials with low ionization levels, there is a relative absence of sulfonate groups near the surface in the air-equilibrated environment of the ATR/FTIR technique. In the absence of sulfonate groups, the urethane carbonyl have to hydrogen-bond to urethane hydrogen atoms in the surface region. The net result is a larger-than-expected proportion of hydrogen-bonded urethane carbonyl groups near the surface.

All of these polymers have approximately the same hard to soft segment ratio in the bulk. As seen in Table II, there is very little change in the hard-to-soft segment absorbance ratio for these materials either in the bulk or within the penetration depth of the ATR technique.

F. ESCA Analysis of the Surface Region

The results of the ESCA analysis of the anionomers of the present invention are shown in Table V, and a comparison of $C_{1S}$ high resolution spectra of several of the materials is shown in FIG. 6. The $C_{1S}$ spectra consist of several well-resolved peaks. The main peak, referenced to 285.0 eV, is due to unsubstituted aliphatic and aromatic carbon atoms. The peak that is shifted approximately 1.5 eV towards the higher binding energy side of the main peak corresponds to carbon atoms that are single-bonded to oxygen atoms. The small peak shifted approximately 5 eV towards the higher binding energy side of the main peak corresponds to carbon atoms that are double-bonded to oxygen atoms in the urethane linkage.

The 286.5 eV "ether" carbon is present in the soft segment and in the urethane linkage. However, the ratio of ether carbon to aliphatic/aromatic carbon in the soft segment is about 0.5, while this ratio for the pure hard segment is about 0.105. Thus, changes in the relative size of the 286.5 eV peak provide an indication of surface hard/soft segment composition. While nitrogen and carbonyl carbons (290 eV) are characteristic of the hard segment, it is known that short hard segment repeat units are mixed into the soft segment phase. The analysis of these materials is aided by the fact that with the exception of sulfur, the bulk elemental composition is virtually identical (constant to within 2 percent) at the level of accuracy of the ESCA technique.

The data presented in Table V show that there are no major differences in the ESCA spectra of these materials. Atomic percentages of carbon, nitrogen, and oxygen are all very similar. Sodium incorporation is not easily detected by the instrument. The level of sulfur, indicative of the ionic group incorporation, is on the same order as the value of 0.7 percent predicted by the stoichiometry for PEU-SO3-0.20. As in the case with sodium, the resolution of the instrument probably is not sufficient to interpret any trends in sulfur incorporation. However, the observed levels of nitrogen and carbonyl carbon were considerably below the value of 4.3 percent for each that is predicted by the stoichiometry.

FIG. 6 shows the $C_{1S}$ high resolution ESCA spectra for polymers PEU, PEU-SO3-0.10 and PEU-SO3-0.20. The curves for PEU and PEU-SO3-0.20 were virtually superimposable, which indicates very similar surface morphologies in vacuo. However, somewhat less ethereal carbon is indicated on PEU-SO3-0.10 than on the other materials. A surface depletion of ethereal carbon is indicated in Table V for the intermediate levels of ion incorporation.

slightly with ionization, but the signals are small, and that observation must be carefully interpreted.

The level of silicon on the surface was not reproducible, even between replicate samples of the same copolymer. This suggests a small, patchy amount of poly(dimethylsiloxane) contamination. As indicated in wettability studies, however, a hydrophobic surface that would be characteristic of a silicone overlayer is not indicated for any of these materials.

In summary, the ESCA data indicate that there is surface soft segment enrichment for all of these polymers. Although some change in the $C_{1S}$ spectra may be observed with low-to-moderate levels of ionization, the similarity between the ESCA spectra of PEU and PEU-SO3-0.20 is striking and indicated that the in vacuo surface chemistry of these materials is similar.

G. Contact Angle Analysis

Contact angle data are shown in Table VI. As the surface polarity of a material increases, the contact angle as measured through the water phase should decrease. The contact angle data indicate that as the level of sulfonation increases, the polyurethanes become much more hydrophilic. In fact, air bubbles do not adhere reproducibly to the surface of PEU-SO3-0.20 when the sample is under water. This behavior is unexpected and unlike what has been observed for other polyurethane systems, including some polyurethane ionomers, examined using the same underwater contact angle technique. The nonadherence of air bubbles to highly polar surfaces is, in fact, a limitation of the underwater contact angle technique when it is used to determine surface energetics, and it indicates that the polar component of the solid surface energy is above 53 dynes/cm.

TABLE V

| | ESCA Analysis of Polyurethane Anionomers | | | | | | | |
|---|---|---|---|---|---|---|---|---|
| | ESCA Atomic Percentage | | | | | | | |
| Polymer | $C_{total}$ | $C_{285eV}$ | $C_{285.5eV}$ | $C_{290e-V}$ | N | O | S | Si |
| PEU | 78 | 46 | 31 | 1.0 | 2.3 | 19 | 0 | 0.4 |
| PEU-SO3-0.05 | 81 | 49 | 31 | 1.1 | 2.2 | 14 | 0.1 | 0.5 |
| PEU-SO3-0.10 | 81 | 57 | 23 | 1.2 | 2.5 | 16 | 0.4 | 0.2 |
| PEU-SO3-0.15 | 80 | 56 | 22 | 1.3 | 2.4 | 17 | 0.6 | 0.3 |
| PEU-SO3-0.20 | 82 | 49 | 31 | 1.5 | 2.5 | 15 | 0.6 | 0.4 |
| SO3-0.15 COO-0.05 | 81 | 49 | 31 | 1.1 | 2.3 | 15 | 0.5 | 1.1 |
| SO3-0.10 COO-0.10 | 83 | 54 | 28 | 1.2 | 2.2 | 14 | 0.2 | 0.8 |

It can be seen in FIG. 6 that the resolution of the peaks was not identical for PEU-SO3-0.10 as for the other polymers, and the process of fitting Gaussian peaks and resolving the spectra of PEU-SO3-0.10 and PEU-SO3-0.15 was made somewhat more difficult. Still, difficulties with curve resolution do not fully explain differences from the base material of 25 percent that were observed. The bulk characterization indicated that copolymers PEU-SO3-0.10 and PEU-SO3-0.15 were more poorly phase-separated than the base material and had a greater degree of hard segment in the soft segment phase. As hard segments become mixed into the soft segment phase, the proportion of aliphatic-/aromatic carbon will increase, and that trend was observed with PEU-SO3-0.10 and PEU-SO3-0.15. Changes in the level of surface nitrogen also increase

TABLE VI

| | Contact Angle/Wettability Data for Polyurethane Ionomers | | | | |
|---|---|---|---|---|---|
| | Underwater Contact Angle Measured Through the | | Surface- | In-Air | |
| | Water Phase: | | Water | Contact | |
| | Surface-water-air | Surface-water-air | Interfacial Energy, | Angle (degrees) | |
| Polyemr | (degrees) | (degrees) | (dyn/cm) | adv. | rec. |
| PEU | 62 ± 7 | 85 ± 8 | 15 | 78 | 63 |
| PEU-SO3-0.05 | 37 ± 3 | 58 ± 5 | 7 | ND | ND |
| PEU-SO3-0.10 | 33 ± 4 | 46 ± 6 | <5 | 60 | 35 |
| PEU-SO3-0.15 | 26 ± 4 | 30 ± 4 | <5 | ND | ND |
| PEU-SO3-0.20 | <10 | 34 ± 4 | <5 | 37 | 37 |
| SO3-0.15 COO-0.05 | <10 | 30 ± 3 | <5 | ND | ND |
| SO3-0.10 COO-0.10 | 17 ± 3 | 39 ± 8 | <5 | ND | ND |

ND = Not Determined

The use of harmonic or geometric mean equations with the underwater captive bubble technique to obtain surface energy values is controversial, and the significance of the actual surface energy values that may be calculated for these polymers may be questionable. However, it is apparent that even the base material has polar character, and the extent of this polarity increases substantially upon ionization. The sharp differences in surface wettability between PEU and PEU-SO3-0.20 are in sharp contrast with the relatively small differences observed between these materials using the in vacuo ESCA technique. The differences between the results of the two techniques suggest that the polyurethane surfaces are mobile and capable of rearranging to minimize their interfacial tension with the environment.

Among the anionomers containing a twenty percent replacement of the urethane hydrogen, it is seen in Table VI that the wettability, although high when compared to the other polymers, decreases as the proportion of carboxylate derivatization is increased. This observation indicates that the highly acidic character of the sulfonate group compared to the carboxylate group contributes to the wettability and perhaps the ability of the functional group to orient toward a water-contacting interface.

The water-in-air advancing and receding contact angles measured inside the coated tubings indicate similar trends and variations. The wettability of the polyurethane is observed to increase strongly upon ionization. The apparent contact angle hysteresis initially increased with ionization and then decreased to a very small level. Since many different phenomena contribute to contact angle hysteresis, it is difficult to separate the different factors which will change the observed hysteresis. For example, scanning electron microscopic examination of the dry surfaces did not reveal visible roughness, but surface molecular mobility, which can affect contact angle hysteresis, may still be present in the hydrated surfaces.

These results do suggest, however, that the presence of ionic groups has a strong effect on both the advancing and receding contact angles. The advancing angle is characteristic of the nonpolar component of a surface, while the receding angle, in the absence of factors such as surface roughness, is especially sensitive to the polar component. Thus, it appears that the dispersive component of the surface disappears upon ionization.

H. Blood Compatibility

A surface is considered to be "thrombogenic" if relatively large numbers of platelets and/or fibrinogen molecules adhere to it. FIGS. 7-10 show platelet and fibrinogen deposition profiles which were determined over the initial hour of blood contact for the polymers of the present invention. Two sets of animal experiments, each set consisting of three different dogs, are performed.

Very different platelet and fibrinogen responses, spanning several orders of magnitude, are observed with these materials. Because of these unexpected results, and because platelet and fibrinogen deposition levels, by necessity, have a lower bound of zero, it is not surprising to observe that symmetric distributions of platelet or fibrinogen deposition around an arithmetic mean for a given material and time point are almost never observed. Thus, for the purposes of data analysis, a logarithmic transform was employed. The mean+SD was then determined, and the data were re-transformed for plotting. Animal-to-animal variation was a significant factor in the first surgery set and may also be expected in a clinical blood-contacting situation. It is very important to note, however, that each animal showed the same trends in thrombus deposition. Thus, it was decided to simplify the data analysis and reporting of data by lumping the animals together from each surgery set in an attempt to see if material variations play a role in the blood-material interactions.

The role of the thrombotic potential of the animal in determining the actual extent of blood-material interactions has been disclosed in the prior art. The dogs used herein were initially prescreened for platelet aggregability to ADP and epinephrine, platelet counts of 150,000–400,000 reciprocal microliters, a fibrinogen levels of 100–300 mg/dl and hematocrit levels of 35–50.

In terms of platelet aggregability, in particular, all animals were well within the acceptable range. During the course of the study, platelet and plasma fibrinogen levels and packed cell volumes remained essentially unchanged. The euglobulin lysis times (ELT), activated thromboplastin time (PTT) and prothrombin times remained unchanged during the course of the experiments, although in one surgery the ELT was somewhat lower than normal. In summary, however, no monitored hematological parameters were found to correlate with the enhanced platelet response of one animal or the low fibrinogen response of the other.

Figure 7:
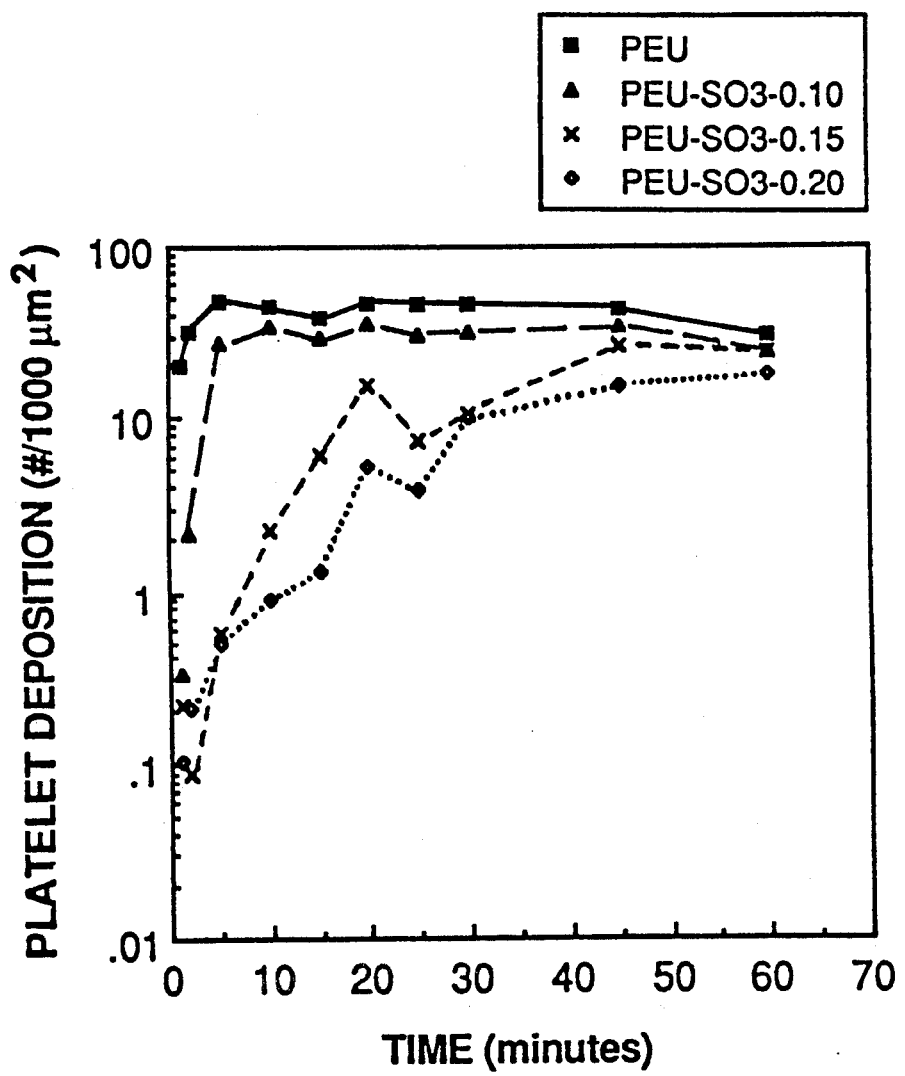
FIGS. 7–10 illustrate platelet and fibrinogen deposition profiles for a polyurethane and for polyurethane ionomers having sulfonate or sulfonate and carboxylate functionality.
Figure 8:
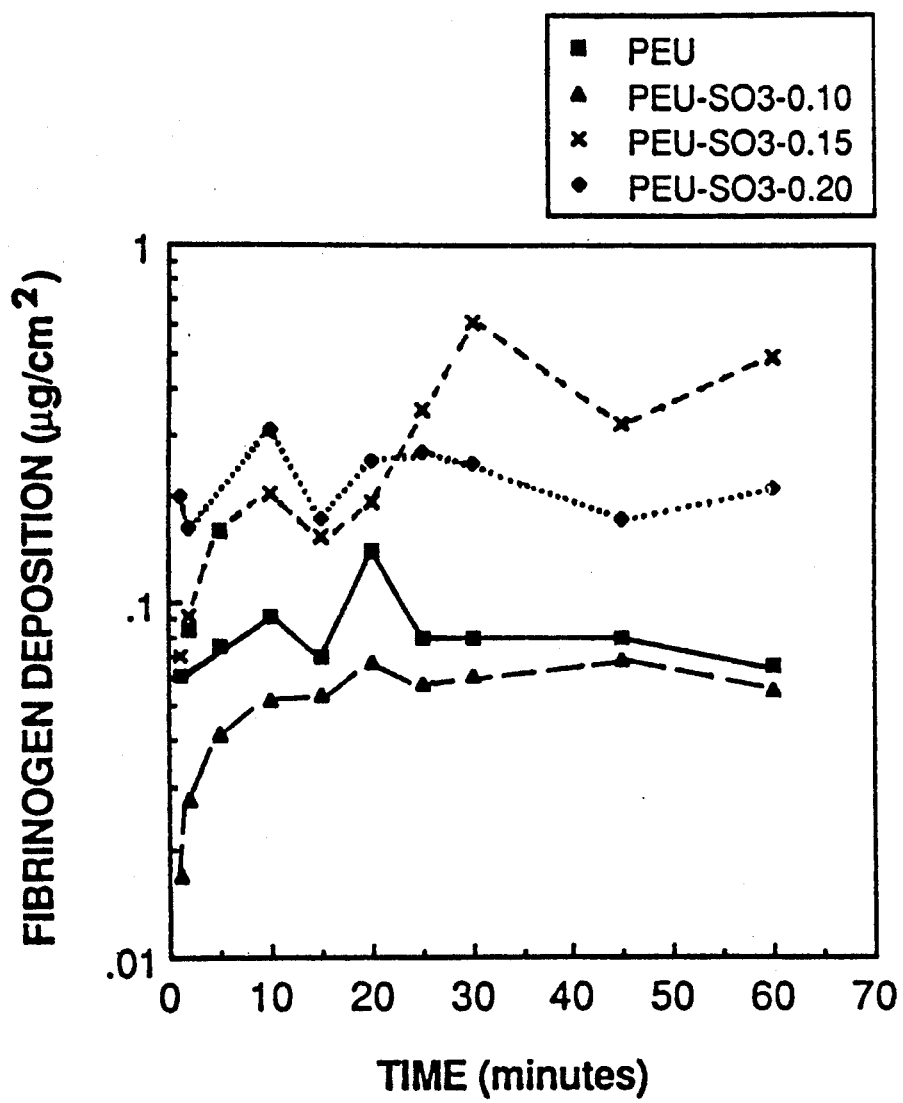

The first set of animal experiments studied the effect of sulfonate incorporation into the polyurethane block copolymer, and the results of the ex vivo animal studies are shown in FIGS. 7 and 8. Table VII contains the results of two-sided t-tests which were performed for selected pairs of surfaces at each time point of blood exposure. At low levels of ionization (PEU-SO3-0.05), there was no significant effect of ion incorporation on platelet deposition, but some significant decreases in platelet deposition were observed at several time points on PEU-SO3-0.10. Platelet deposition decreased as ionic content was further increased. The mean platelet deposition levels observed for PEU-SO3-0.15 and PEU-SO3-0.20, at under 10 platelets/1000 $m^2$ for 30 minutes of blood exposure, are lower than previously seen for any other tested material in the same ex vivo blood-contacting experiment.

TABLE VII

| Materials Being Compared | Platelets or Fibrinogen | Statistical Analysis of Ex Vivo Animal Surgery Results | | | | | | | |
|---|---|---|---|---|---|---|---|---|---|
| | | Time point of Comparison (min.) | | | | | | | |
| | | 5 | 10 | 15 | 20 | 25 | 30 | 45 | 60 |
| PEU & PEU-SO3-0.10 | platelet | +++ | − | − | + | + | + | − | − |
| (SET #1) | fibrinogen | ++ | − | − | ++ | − | − | − | − |
| PEU & | platelet | +++ | +++ | ++ | ++ | ++ | ++ | − | − |
| SO3-.1 COO-.1 & | platelet | − | +++ | +++ | +++ | +++ | ++ | − | − |

TABLE VII-continued

| Materials Being Compared | Platelets or Fibrinogen | Statistical Analysis of Ex Vivo Animal Surgery Results Time point of Comparison (min.) | | | | | | | |
|---|---|---|---|---|---|---|---|---|---|
| | | 5 | 10 | 15 | 20 | 25 | 30 | 45 | 60 |
| SO3-.15 COO-.05 | fibrinogen | +++ | +++ | +++ | +++ | +++ | +++ | +++ | +++ |

Key for Table VII:
+++ Null hypothesis (that mean deposition levels for the materials being compared are identical) may be rejected with 99.9 percent level of confidence.
++ Null hypothesis may be rejected at 99 percent confidence level.
+ Null hypothesis may be rejected at 90 percent confidence level.
− Null hypothesis may not be rejected at 90 percent confidence level or higher.

FIG. 8 shows the fibrinogen deposition profiles for the ionized polyurethanes. The fibrinogen deposition profile for PEU-SO3-0.05 (not shown) is comparable to that of PEU. This indicates no significant effects of low ionization levels. This observation is interesting in light of the significantly higher wettability of PEU-SO3-0.05 as compared to PEU. Increasing the sulfonation level to that of PEU-SO3-0.10 resulted in decreased mean fibrinogen deposition levels at each blood contact time.

Table VII indicates, however, that when each time point is individually considered, the difference between the PEU-SO3-0.10 ionomer and PEU was only significant at two time points. The lack of significance is attributed to the inter-animal variation and the global data analysis, but if the animals are considered individually, a significant decrease in fibrinogen deposition onto PEU-SO3-0.10 is observed as compared to PEU. This trend has been disclosed in prior art references which indicate that platelet and fibrinogen deposition both decreased when propyl sulfonate functionality was incorporated into PTMO-based polyurethane block copolymers which were chain-extended with N-methyldiethanolamine.

Higher levels of ionization resulted in significant increases in fibrinogen deposition, as shown in FIG. 8 and in Table VII. Fibrinogen deposition onto PEU-SO3-0.15 and PEU-SO3-0.20 was higher than on PEU or the other materials at all time points of blood exposure. Due to the inter-animal variations, it was impossible to distinguish between these two materials. Results from the second surgery set confirmed the highly significant increase in fibrinogen deposition on copolymer PEU-SO3-0.20. This result was surprising and unexpected because the platelet and fibrinogen deposition results of the prior art indicate that the trends in the magnitudes of platelet and fibrinogen deposition for polyurethane ionomers, along with polyurethanes and other polymers, tend to parallel each other. The present invention represents the first occurrence of low platelet deposition being accompanied with unusually high fibrinogen deposition levels in the canine ex vivo model.

Another significant difference between the behavior of the present copolymers and prior materials is that the initial platelet deposition rates onto PEU-SO3-0.15 and PEU-SO3-0.20 were very low, in contrast with the polyurethane zwitterionomer and anionomer where deposition levels of nearly 50 platelets/1000 m² were seen after only two minutes of blood exposure.

Scanning electron micrographs of platelets adhering to these polyurethane surfaces showed differences in the platelet-surface interactions depend upon the ionic content of the polymer. Platelets adherent on the polyethylene reference material showed a tendency to spread on the surface, and many small platelet thrombi are seen on polyethylene compared to well-phase-separated polyurethane block copolymers (Lelah et al., in *Polymers as Biomaterials*, Plenum Press. New York, 257 (1984); Grasel et al., *Biomaterials*, 7, 315 (1987).

Figure 11:
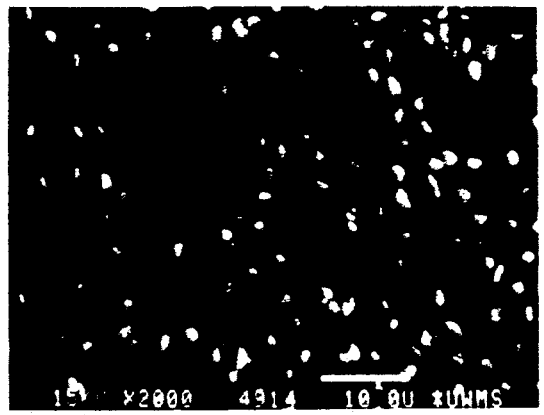
FIG. 11 illustrates platelet adherence to a non-ionized polyurethane surface as a function of blood exposure time.
Figure 11:
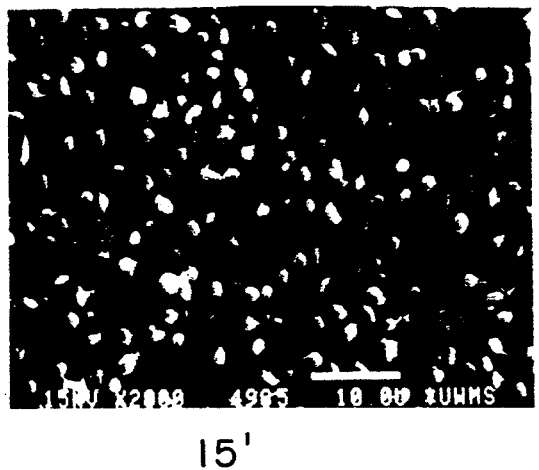
Figure 11:
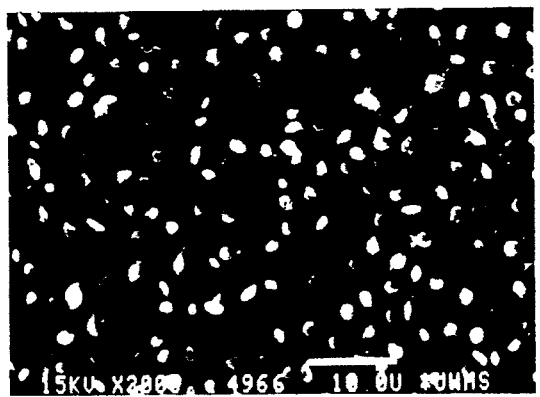
Figure 11:
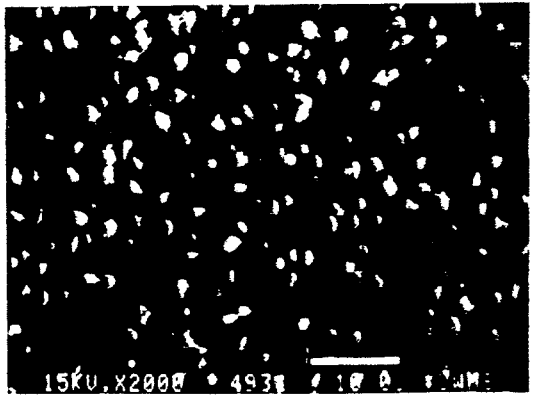

FIG. 11 shows platelets adherent on PEU at blood exposure time of 5, 15, 30 and 60 minutes. These platelets show some pseudopod extension and platelet shape-change, but very little platelet spreading, in agreement with previous observations on the same material.

Figure 12:
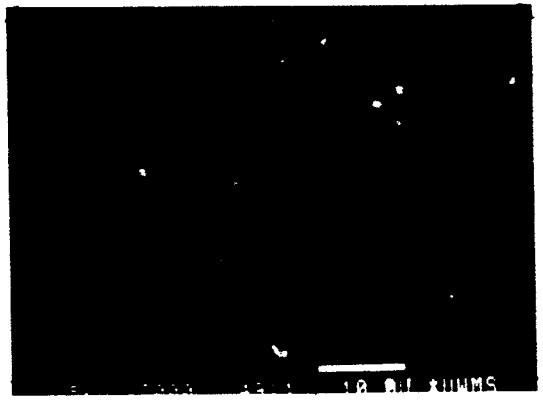
FIG. 12 illustrates platelet adherence to a polyurethane surface having moderate sulfonate functionality as a function of blood exposure time.
Figure 12:
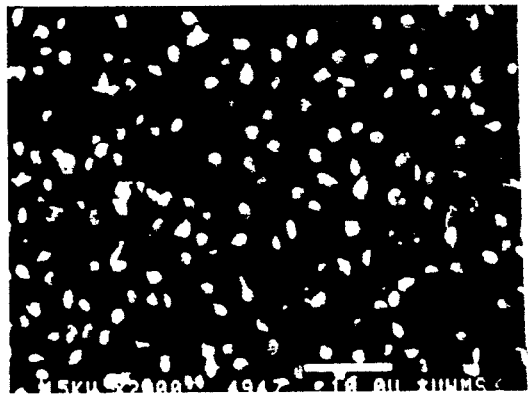
Figure 12:
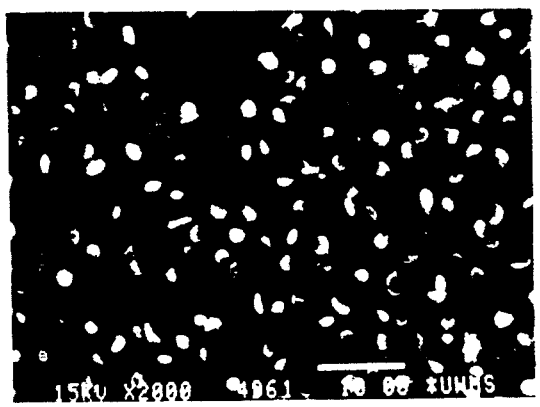
Figure 12:
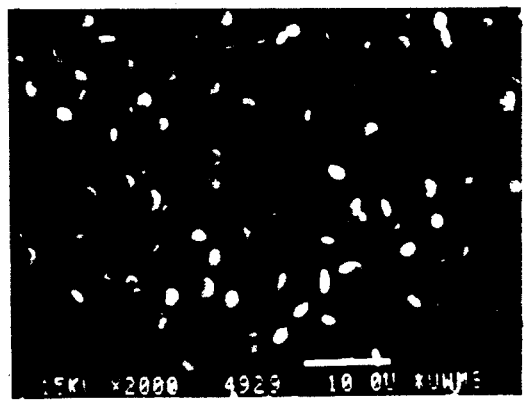

Platelets adherent on PEU-SO3-0.10 are shown in FIG. 12 for the same blood exposure times. In agreement with the platelet deposition profiles of FIG. 7, relatively few platelets are seen on this material as compared to PEU, especially at 5 and 60 minutes. Although the platelet numbers are similar to those on PEU at 15 and 30 minutes of blood exposure, platelets on PEU-SO3-0.10 show significantly less pseudopod extension and appear much rounder than those on PEU. The platelet morphologies observed at 15 minutes on PEU-SO3-0.10 are very similar to those observed in the prior art on a polyurethane zwitterionomer. However, the platelets adherent at 60 minutes on this material are considerably rounder than those found on the zwitterionomer.

Figure 13:
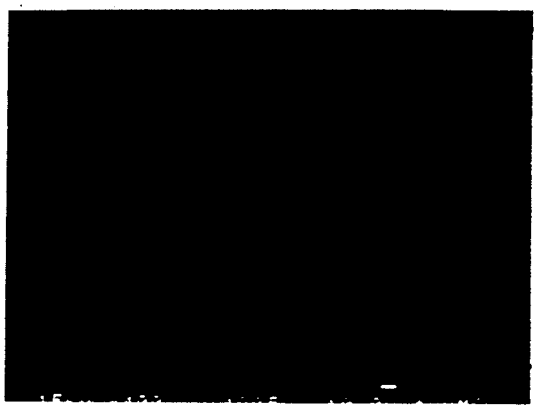
FIG. 13 illustrates platelet adherence to a polyurethane surface having high sulfonate functionality as a function of blood exposure time.
Figure 13:
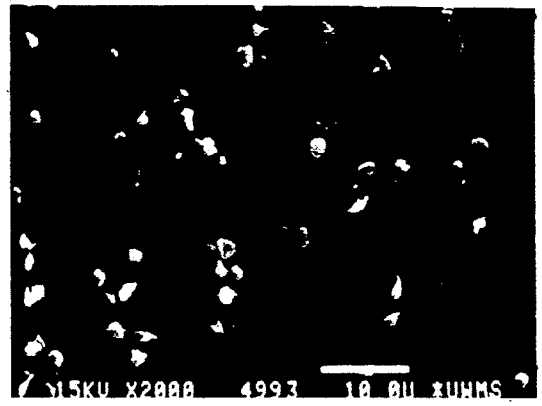
Figure 13:
Figure 13:
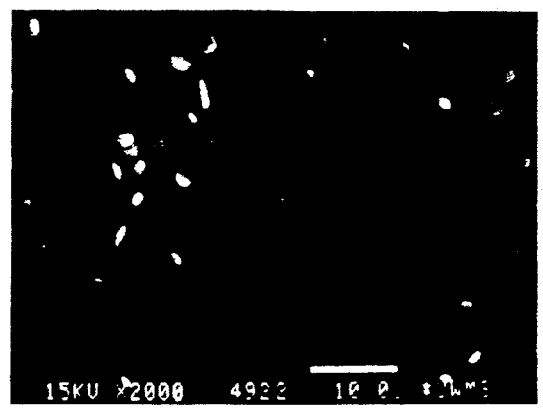

The most striking scanning electron micrographs were of PEU-SO3-0.15 and PEU-SO3-0.20, as indicated by the micrographs adherent on the latter of these materials in FIG. 13. After 5 minutes of blood exposure, there were virtually no adherent platelets on this material. This is in agreement with the platelet deposition curves obtained by radiolabeling studies. Some platelets are observed at longer exposure times, but large bare patches are also observed. This unusual behavior has not been observed previously in the ex vivo experiment. The adherent platelets are very round and generally not pseudopodial, although the micrograph at 15 minutes of blood exposure shows some pseudopodia that are interacting with other pseudopodia and platelets.

No significant fibrin formation was observed on these ionized surfaces by scanning electron microscopy, but it should be noted that fibrin is rarely observed in the canine ex vivo arteriovenous shunt configuration operating at shear rates on the order of 1000 sec⁻¹ and above.

Figure 14:
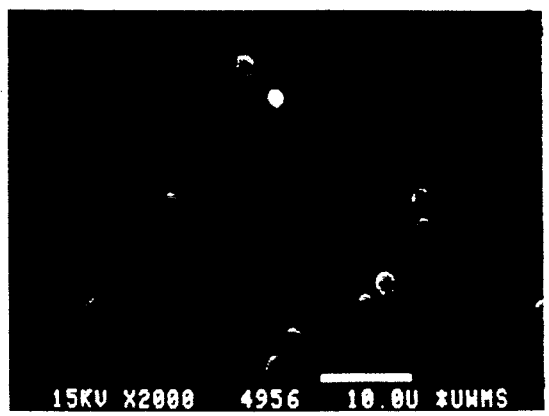
FIG. 14 illustrates platelet adherence to a polyurethane surface having a moderately high sulfonate functionality after exposure to blood for 30 minutes.
Figure 14:
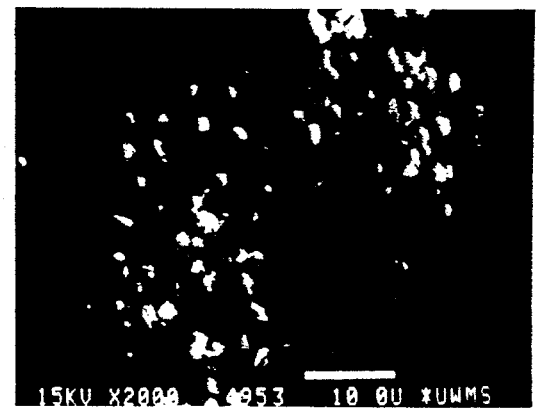

Although the mean platelet deposition levels for PEU-SO3-0.15 and -0.20 begin to approach those of the other polyurethanes at 60 minutes of blood exposure, the platelet morphologies are strikingly different on the polyurethane anionomers. When platelets are adherent on a surface, as shown in FIG. 14b for PEU-SO3-0.15 after 30 minutes of exposure to blood, the platelets tended to be in groups of platelets adherent to and interacting with each other, instead of with the surface. The platelets forming the base of the thrombus in FIG. 14b are spread over the surface. The cause of this thrombus was most likely a dust particle or coating imperfection or other random event of the same type often seen with other materials.

Figure 9:
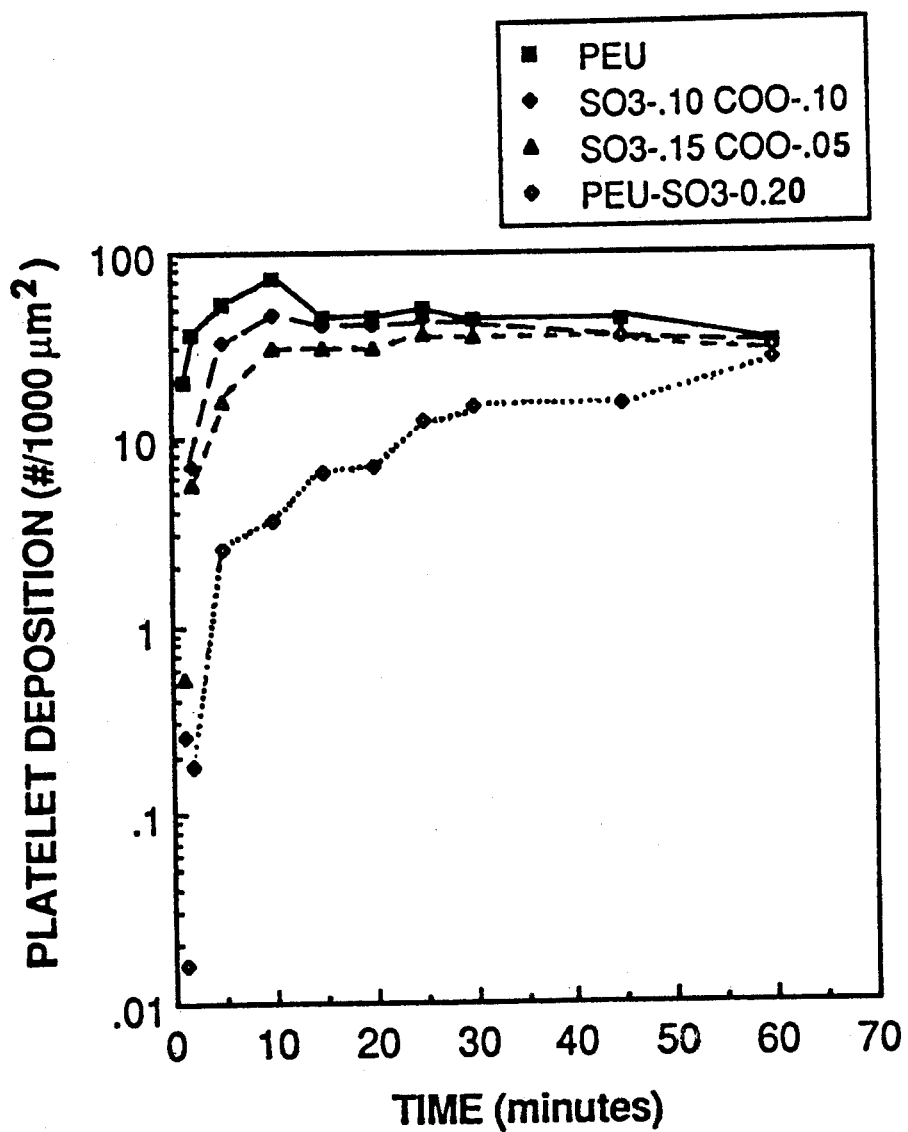
Figure 10:
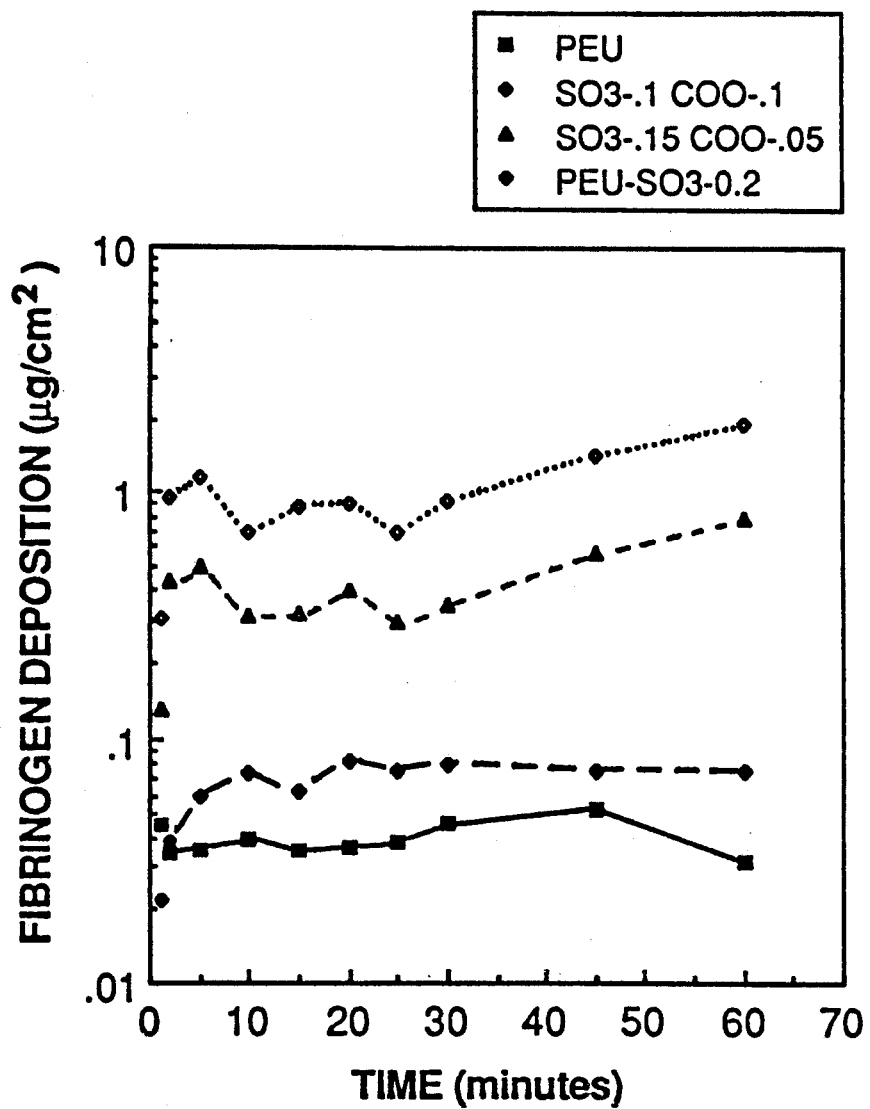

Platelet and fibrinogen deposition profiles for the second surgery set are shown in FIGS. 9 and 10 for PEU, PEU-SO3-0.20, and the carboxylated analogs of the latter copolymer. The same trends in platelet and fibrinogen deposition are observed between PEU and PEU-SO3-0.20, and in fact the trends are more pronounced here than in the first series of animal experiments due to minimal inter-animal variations. The actual differences in the deposition levels between the two surgery sets were probably due to animal-to-animal variations within each surgery set.

As the sulfonate level increases, the mean platelet deposition levels decrease, as shown in FIG. 9. Thus, the presence of sulfonate and not the presence of ionic species appears to affect platelet deposition onto these polyurethanes. Similarly, fibrinogen deposition appears to be related, almost logarithmically, to the percentage of sulfonate incorporation into the copolymer, with the carboxylate groups appearing to have less effect. A small effect may be indicated by the fact that fibrinogen deposition is enhanced on PEU-SO3-0.1 COO-0.1 as compared to PEU. The same trend is not observed for PEU-SO3-0.1 COO-0.1 as compared to PEU, or for PEU-SO3-0.1 as compared to PEU in the first surgery set.

Because of the similarity of the ex vivo results of those polymers, however, it is difficult to quantify the effect of carboxylate functionality on platelet and fibrinogen deposition. The effect, however, is not as significant as the effect of incorporating sulfonate functionality into the polyurethane block copolymer.

I. POSSIBLE MECHANISMS OF THE SULFONATED POLYURETHANE-BLOOD INTERACTION

As previously noted, it is surprising that highly sulfonated surfaces show little platelet adhesion and activation, and at the same time shown high levels of fibrinogen deposition. Previously, it was generally believed that the ability of a polymer surface to promote platelet adhesion and activation is correlated with the amount of adsorbed or deposited fibrinogen. The binding of fibrinogen to a surface from blood or whole plasma is a complex process that involves competition with a number of other plasma proteins over a short period of time. In the absence of other proteins, the amount of adsorbed fibrinogen in a monolayer can range from 0.21 $g/cm^2$ for side-on adsorption to 1.57 $g/cm^2$ for end-on adsorption. It is improbable that materials such as PEU-SO3-0.2 adsorb fibrinogen to the exclusion of every other protein, so that some multi-layer adsorption or absorption of fibrinogen is likely.

It is known that albumin, which is negatively charged at pH 7.4, adsorbs more slowly to a negative-charged surface than to a positively-charged surface. The electrokinetic effect of albumin adsorption may permit a protein such as fibrinogen to adsorb more rapidly to a negatively-charged surface. Conversely, it has also been found that an anionic polyurethane selectively adsorbed albumin from competitive adsorption experiments. However, previous studies did not report large charge-related effects on fibrinogen adsorption behavior.

The preferential adsorption of fibrinogen to the PEU-SO3-0.20 anionomer has been examined in in vitro adsorption studies from both heparinized and citrated whole blood. Peak plateau levels of fibrinogen deposition on the order of 2 or more $g/cm^2$ were measured in both cases. In simple fibrinogen adsorption from buffer, the same trend in fibrinogen adsorption was detected.

It is possible that fibrinogen molecules are being absorbed to some extent in the water-containing hydrogels. However, there still is a reduced level of platelet attachment and activation at the surface. An explanation of these trends may be related to the configuration and/or conformation of the adsorbed fibrinogen that is on the surface. Prior studies have examined the differences in platelet retention and activation on polyalkyl methacrylates which had similar fibrinogen binding characteristics. It was found that differences in binding affinities of adsorbed fibrinogen molecules for fibrinogen antibody, as opposed to the total number of adsorbed fibrinogen molecules, correlated with "platelet reactivity".

Further studies have indicated that the conformation of adsorbed fibrinogen molecules, as opposed to differences in the orientation of the adsorbed fibrinogen, is the primary determinant of the anti-fibrinogen binding to the fibrinogen adsorbed on these materials. All of the prior art appears to lead to the conclusion that fibrinogen molecules bound to a surface in an undistorted, "native" conformation are required for platelet activation by surfaces to occur. In the polymers of the present invention, however, the ionic surfaces may be inducing a conformational change in the fibrinogen molecule which may reduce or prevent platelet attachment or activation.

As demonstrated herein, the incorporation of sulfonate and carboxylate groups into a polyurethane block copolymer exerts an effect on bulk properties, surface chemistry, and blood compatibility as measured in an acute canine ex vivo blood-contacting experiment.

Bulk physical property testing including differential scanning calorimetry, dynamic mechanical testing, and infrared spectroscopy indicate variations in bulk morphology as the ionic content is changed. Initially, at low levels of ion incorporation, phase separation decreases as the hard segments become more disordered, but phase separation improves as the ionic content is further raised. The water sensitivity of the present ionic polymers may limit their application in certain environments, and the high-temperature performance appears poorer for the anionomers than for the base material.

ESCA data collected in vacuo indicates surface soft segment enrichment and nearly identical surface chemistry for all of the present polymers materials, but contact angle/wettability data show major differences for these polymers, with wettability increasing with ionic content.

Blood compatibility data clearly indicates that as the level of sulfonate incorporation is increased, platelet attachment and platelet spreading and activation decrease substantially. The unusual phenomenon of increased fibrinogen deposition on the sulfonated polymers, when compared to the uncharged base polymer, indicates conformational changes in the fibrinogen molecules upon adsorption which renders the surface non-platelet-activating. Carboxylate incorporation into the copolymers of this invention has an effect in increasing fibrinogen deposition, but the effect of sulfonate incorporation is more pronounced.

While the present invention has been described with reference to particular embodiments, it will be understood that various changes and modifications can be made without departing from the spirit of the invention.

What is claimed is:

1. A biocompatible device having at least one surface which includes a polyether-polyurethane copolymer based on a mole ratio of about 1.5/0.5/1.0 to about 10/9/1 of an organic diisocyanate, a $C_2$–$C_{14}$ alkyl or aryl diol or diamine and a polyol having a number average molecular weight from about 500 to about 3000, the copolymer being modified wherein about 5 to about 25 percent of the urethane hydrogen atoms are replaced with a combination of lower alkyl ($C_1$–$C_6$) sulfonate groups and lower alkyl ($C_1$–$C_6$) carboxylate groups.

2. The device of claim 1 wherein said organic diisocyanate is selected from the group consisting of 2,4-toluene diisocyanate, 2,6-toluene diisocyanate, methylene bis(p-phenyl isocyanate), 1,5-naphthalene diisocyanate, methylene bis(p-cyclohexyl isocyanate), 1,6-hexane diisocyanate, isophorone diisocyanate and cyclohexyl diisocyanate.

3. The device of claim 1 wherein said diol or diamine is selected from the group consisting of 1,4-butanediol, ethylene diamine, 4,4′-methylene bis(2-chloroaniline), ethylene glycol and hexanediol.

4. The device of claim 1 wherein said polyol is selected from the group consisting of polyethylene oxide, polypropylene oxide, polytetramethylene oxide, polyisobutylene, polybutadiene, polyethylene adipate, polytetramethylene adipte, polycaprolactone and polydimethylsiloxane.

5. A biocompatible device for biomedical applications including surgical implantations, blood contacting procedures and the like, said device comprising a polyurethane composition which includes a polyether-polyurethane copolymer based on a mole ratio of about 1.5/0.5/1.0 to about 10/9/1 of (a) an organic diisocyanate, (b) a $C_2$–$C_{14}$ alkyl or aryl diol or diamine and (c) a polyol having a number average molecular weight from about 500 to about 3000, the copolymer being modified wherein about 5 to about 25 percent of the urethane hydrogen atoms are replaced with a combination of propyl sulfonate groups and propyl carboxylate groups.

6. The device of claim 5 wherein said organic diisocyanate is selected from the group consisting of 2,4-toluene diisocyanate, 2,6-toluene diisocyanate, methylene bis(p-phenyl isocyanate), 1,5-naphthalene diisocyanate, methylene bis(p-cyclohexyl isocyanate), 1,6-hexane diisocyanate, isophorone diisocyanate and cyclohexyl diisocyanate.

7. The device of claim 5 wherein said diol or diamine is selected from the group consisting of 1,4-butanediol, ethylene diamine, 4,4′-methylene bis(2-chloroaniline), ethylene glycol and hexanediol.

8. The device of claim 5 wherein said polyol is selected from the group consisting of polyethylene oxide, polypropylene oxide, polytetramethylene oxide, polyisobutylene, polybutadiene, polyethylene adipate, polytetramethylene adipate, polycaprolactone and polydimethylsiloxane.

9. A biocompatible device having a blood- or tissue-containing portion comprising a poly(tetramethylene oxide) -based polyurethane composition which comprises a polyether-polyurethane copolymer based on a 3/2/1 mole ratio of an organic diisocyanate, a $C_2$–$C_{14}$ alkyl or aryl diol or diamine and a polytetramethylene oxide having a number average molecular weight of about 1000, the copolymer being modified wherein about 5 to about 25 percent of the urethane hydrogen atoms are replaced with a combination of propyl sulfonate groups and propyl carboxylate groups.

10. The device of claim 9 wherein said organic diisocyanate is selected from the group consisting of 2,4-toluene diisocyanate, 2,6-toluene diisocyanate, methylene bis(p-phenyl isocyanate), 1,5-naphthalene diisocyanate, methylene bis(p-cyclohexyl isocyanate), 1,6-hexane diisocyanate, isophorone diisocyanate and cyclohexyl diisocyanate.

11. The device of claim 9 wherein said diol or diamine is selected from the group consisting of 1,4-butanediol, ethylene diamine, 4,4′-methylene bis(2-chloroaniline), ethylene glycol and hexanediol.

12. A device for biomedical use comprising a poly(tetramethylene oxide)-based polyurethane composition which comprises a polyether-polyurethane copolymer based on a 3/2/1 mole ratio of methylene bis(p-phenyl isocyanate), 1,4-butanediol and polytetramethylene oxide having a number average molecular weight of about 1000, the copolymer being modified wherein about 5 to about 25 percent of the urethane hydrogen atoms are replaced with a combination of propyl sulfonate groups and propyl carboxylate groups.

* * * * *